(12) United States Patent
Murakita

(10) Patent No.: US 10,306,151 B2
(45) Date of Patent: May 28, 2019

(54) IMAGE PROCESSING DEVICE, IMAGE PROCESSING METHOD, PROGRAM AND IMAGE PROCESSING SYSTEM

(71) Applicant: SONY CORPORATION, Tokyo (JP)

(72) Inventor: Masashi Murakita, Chiba (JP)

(73) Assignee: SONY CORPORATION, Tokyo (JP)

( * ) Notice: Subject to any disclaimer, the term of this patent is extended or adjusted under 35 U.S.C. 154(b) by 35 days.

(21) Appl. No.: 15/541,269

(22) PCT Filed: Nov. 17, 2015

(86) PCT No.: PCT/JP2015/082271
§ 371 (c)(1),
(2) Date: Jun. 30, 2017

(87) PCT Pub. No.: WO2016/129160
PCT Pub. Date: Aug. 18, 2016

(65) Prior Publication Data
US 2017/0366724 A1    Dec. 21, 2017

(30) Foreign Application Priority Data

Feb. 12, 2015  (JP) ................................. 2015-025134
Feb. 12, 2015  (JP) ................................. 2015-025135

(51) Int. Cl.
*H04N 5/235* (2006.01)
*A61B 1/04* (2006.01)
(Continued)

(52) U.S. Cl.
CPC ............ *H04N 5/2351* (2013.01); *A61B 1/04* (2013.01); *A61B 1/06* (2013.01); *G02B 23/2469* (2013.01);
(Continued)

(58) Field of Classification Search
CPC .. H04N 5/2351; H04N 5/2256; H04N 5/2353; A61B 1/04; A61B 1/06; G02B 23/24; G02B 23/26
See application file for complete search history.

(56) References Cited

U.S. PATENT DOCUMENTS

2010/0021028 A1*  1/2010  Kiyuna ............. G01N 21/6428
                                                          382/128
2014/0085473 A1*  3/2014  Donishi ................... B60R 1/00
                                                          348/148

(Continued)

FOREIGN PATENT DOCUMENTS

JP       5-164976 A       6/1993
JP       2011-076198 A    4/2011

OTHER PUBLICATIONS

International Search Report dated Feb. 16, 2016 in PCT/JP2015/082271.

*Primary Examiner* — Hunter B Lonsberry
(74) *Attorney, Agent, or Firm* — Oblon, McClelland, Naier & Neustadt, L.L.P.

(57) ABSTRACT

[Object] It is desirable to provide a technology capable of further appropriately adjusting the luminance of the endoscopic image.
[Solution] Provided is an image processing device including: a peak detection unit configured to detect a first peak and a second peak in sequence from a high luminance side from a number-of-pixel distribution for each luminance of an endoscopic image based on imaging by an image sensor; and an exposure control unit configured to perform exposure control on a basis of a first luminance difference between the first peak and the second peak.

16 Claims, 14 Drawing Sheets

(51) Int. Cl.
*G02B 23/26* (2006.01)
*A61B 1/06* (2006.01)
*H04N 5/225* (2006.01)
*G02B 23/24* (2006.01)

(52) U.S. Cl.
CPC ........... *G02B 23/26* (2013.01); *H04N 5/2256* (2013.01); *H04N 5/2353* (2013.01); *H04N 2005/2255* (2013.01)

(56) References Cited

U.S. PATENT DOCUMENTS

| | | | |
|---|---|---|---|
| 2015/0116582 A1* | 4/2015 | Yoshikawa | H04N 5/2353 348/362 |
| 2015/0215493 A1* | 7/2015 | Du | G06T 5/40 358/453 |

* cited by examiner

IMAGE PROCESSING DEVICE, IMAGE PROCESSING METHOD, PROGRAM AND IMAGE PROCESSING SYSTEM

TECHNICAL FIELD

The present disclosure relates to an information processing device, an information processing method, a program and an image processing system.

BACKGROUND ART

In recent years, image processing devices for processing an endoscopic image based on imaging by an image sensor have gained in popularity (e.g., see Patent Literature 1). Meanwhile, in a case where an object with higher luminance than inside of a human body (e.g., forceps, gauze or the like) is reflected as a subject, a phenomenon may occur in which the endoscopic image is partially brightened. In particular, the endoscopic images are generally captured in a situation that the light source unit and the image sensor are close to each other, or in a situation that the light source unit and the subject are close to each other, so that such a phenomenon is likely to occur. Hereinafter, an area partially brightened by a reflection of such an object with high luminance in the endoscopic image is also simply referred to as "white area".

CITATION LIST

Patent Literature

Patent Literature 1: JP 2013-42998A

DISCLOSURE OF INVENTION

Technical Problem

Here, due to the occurrence of the white area in the endoscopic image, there is a case where exposure control may be performed so that the luminance of the endoscopic image becomes excessively low. Thus, an observation area may become excessively dark. Accordingly, it is desirable to provide a technology capable of further appropriately adjusting the luminance of the endoscopic image.

Solution to Problem

According to the present disclosure, there is provided an image processing device including: a peak detection unit configured to detect a first peak and a second peak in sequence from a high luminance side from a number-of-pixel distribution for each luminance of an endoscopic image based on imaging by an image sensor; and an exposure control unit configured to perform exposure control on a basis of a first luminance difference between the first peak and the second peak.

According to the present disclosure, there is provided an image processing method including: detecting a first peak and a second peak in sequence from a high luminance side from a number-of-pixel distribution for each luminance of an endoscopic image based on imaging by an image sensor; and performing exposure control by a processor on a basis of a first luminance difference between the first peak and the second peak.

According to the present disclosure, there is provided a program for causing a computer to function as an image processing device including: a peak detection unit configured to detect a first peak and a second peak in sequence from a high luminance side from a number-of-pixel distribution for each luminance of an endoscopic image based on imaging by an image sensor; and an exposure control unit configured to perform exposure control on a basis of a first luminance difference between the first peak and the second peak.

According to the present disclosure, there is provided an image processing system including: a light source unit configured to emit light; an image sensor configured to capture an endoscopic image by receiving reflected light of the light emitted by the light source unit; and an image processing device including a peak detection unit configured to detect a first peak and a second peak in sequence from a high luminance side from a number-of-pixel distribution for each luminance of the endoscopic image, and an exposure control unit configured to perform exposure control on a basis of a first luminance difference between the first peak and the second peak.

Advantageous Effects of Invention

As described above, according to the present disclosure, a technology capable of further appropriately adjusting luminance of an endoscopic image is provided. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
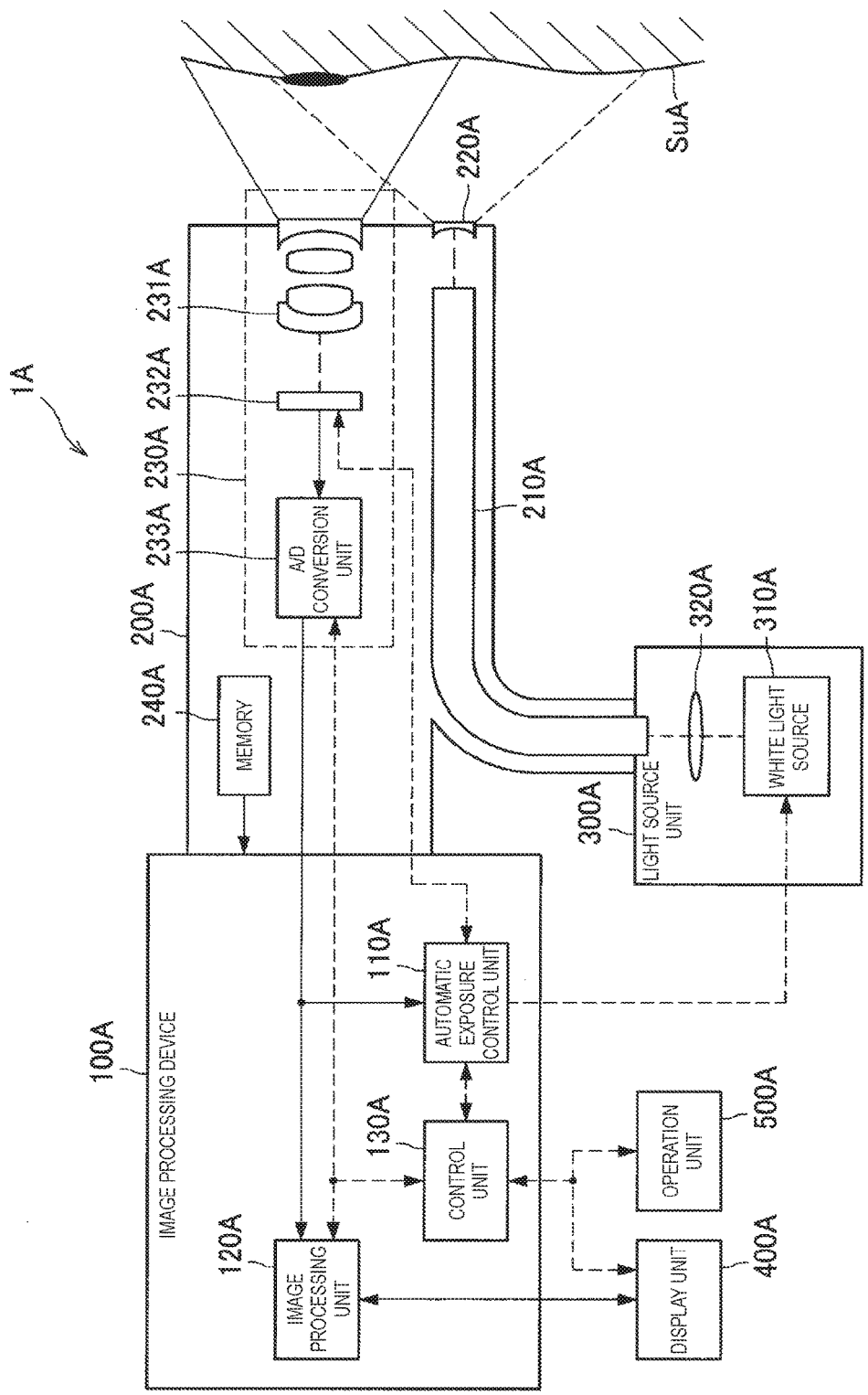
FIG. 1 is a diagram showing an exemplary configuration of an image processing system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that, in this description and the drawings, structural elements that have substantially the same function and structure are sometimes distinguished from each other using different alphabets after the same reference sign. However, when there is no need in particular to distinguish structural elements that have substantially the same function and structure, the same reference sign alone is attached.

Note that description will be given in the following order.
1. Embodiment of the Present Disclosure
   1.1. Exemplary system configuration
   1.2. Exemplary function configuration
   1.3. Functional detail of automatic exposure control unit
2. Conclusion

1. EMBODIMENT OF THE PRESENT DISCLOSURE

1.1. Exemplary System Configuration

First, an exemplary configuration of an image processing system according to an embodiment of the present disclosure will be described with reference to the drawings. FIG. 1 is a diagram showing an exemplary configuration of an image processing system according to an embodiment of the present disclosure. As shown in FIG. 1, the image processing system 1A includes an image processing device 100A, an insertion unit 200A, a light source unit 300A, a display unit 400A, and an operation unit 500A.

The light source unit 300A includes a white light source 310A and a condenser lens 320A. The white light source 310A emits white light. Note that this specification mainly describes examples of using white light, but the color of light is not limited in particular. Accordingly, instead of the white light source 310A, light sources which emit visible light other than white may be used. The condenser lens 320A focuses the light emitted by the white light source 310A to a light guide 210A described below.

The insertion unit 200A can correspond to a scope to be inserted into a body. Specifically, the insertion unit 200A may be a rigid endoscope or a soft endoscope. The insertion unit 200A includes the light guide 210A, an illumination lens 220A, an imaging unit 230A, and a memory 240A. The imaging unit 230A includes an objective lens 231A, an image sensor (imaging element) 232A, and an A/D (analog/digital) conversion unit 233A.

The light guide 210A guides the light focused by the light source unit 300A to the end of the insertion unit 200A. The illumination lens 220A diffuses the light that has been guided to the end by the light guide 210, and irradiates an observation target (subject SuA) with the diffused light. The objective lens 231A focuses the reflected light returning from the observation target (subject Su) to form an image on the image sensor 232A. The image sensor 232A outputs analog signals (endoscopic image) captured by receiving the reflected light to the A/D conversion unit 233A.

Note that the image sensor 232A has, for example, a primary color Bayer array. In such a case, the endoscopic image obtained by the image sensor 232A is a primary color Bayer image. The primary color Bayer image is an image in which each pixel has any of R, G, and B signals, and the RGB pixels are arranged in a staggered pattern. However, the image sensor 232A is not limited to the primary color Bayer array. Namely, the endoscopic image is not limited to the primary color Bayer image. For example, the endoscopic image may be an image acquired by an endoscope imaging method e.g., complementary-color method or frame-sequential imaging method other than the primary color Bayer.

The A/D conversion unit 233A converts, on the basis of a control signal output from a control unit 130 described below, analog signals (endoscopic image) output from the image sensor 232A into digital signals, and outputs the digital signals (endoscopic image) to the image processing device 100A. The memory 240A stores a program for implementing function of the image processing device 100A when being executed by an operation device (not shown).

Note that in the following description, the insertion unit 200A may be referred to as "scope" as appropriate. A different scope can be used for endoscopic diagnosis depending on a diagnosis region. An identification number for specifying a target diagnosis region and a function, such as a zoom function, is assigned to each scope, and in this specification, the identification number may be referred to as "scope ID". The memory 240A stores the scope ID.

The image processing device 100A includes an automatic exposure control unit 110A, an image processing unit 120A, and the control unit 130A. The endoscopic image acquired by the imaging unit 230A is output to the automatic exposure control unit 110A and the image processing unit 120A. The automatic exposure control unit 110A is connected to the white light source 310A and the image sensor 232A, and controls the white light source 310A and the image sensor 232A. The image processing unit 120A is connected to the display unit 400A. The control unit 130A is bidirectionally connected to the imaging unit 230A, the image processing unit 120A, the display unit 400A, and the operation unit 500A, and controls these components.

The automatic exposure control unit 110A automatically performs exposure control of the image sensor 232A such that the luminance of the endoscopic image acquired by the imaging unit 230A is a value appropriate for observation (hereinafter, referred to as "appropriate value"). The automatic exposure control unit 110A will be described in detail below. The image processing unit 120A performs image processing on the endoscopic image captured by the imaging unit 230A. The image processing unit 120A performs, for example, a tone transformation process and a noise reduction process. The image processing unit 120A outputs the image subjected to the image processing to the display unit 400A.

The control unit 130A is connected to the imaging unit 230A, the image processing unit 120A, the display unit 400A, and the operation unit 500A, and outputs control signals for controlling these. The display unit 400A outputs the endoscopic image output by the image processing unit 120A to an image display device such as an endoscope monitor. The operation unit 500A is an interface for receiving operations from a user. For example, the operation unit 500A includes a power switch for turning ON/OFF the power supply, a shutter button for starting an imaging operation, a mode switch button for switching an imaging mode and other various modes, and the like.

The exemplary configuration of the image processing system 1A according to the embodiment of the present disclosure has been described above.

1.2. Example of Exposure Control

Figure 2:
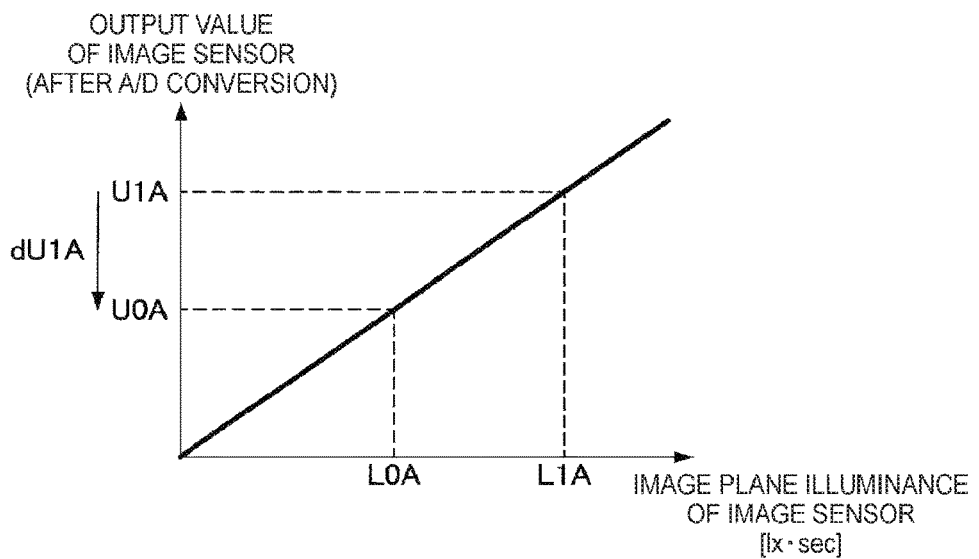
FIG. 2 is an explanatory graph of the specific example of exposure control.
Figure 3:
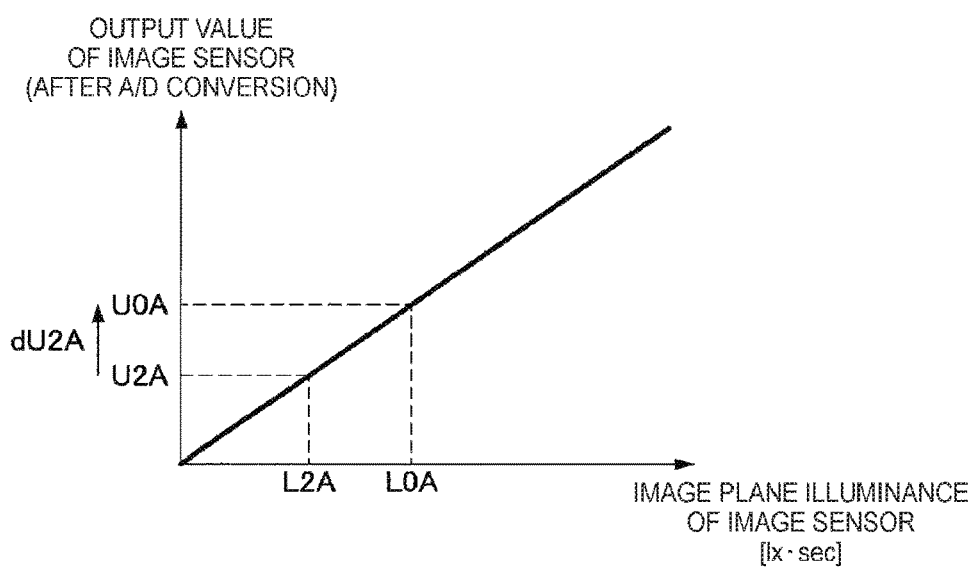
FIG. 3 is an explanatory graph of the specific example of exposure control.

Subsequently, specific examples of exposure control by the automatic exposure control unit 110A will be described. FIGS. 2 and 3 are explanatory graphs of specific examples of the exposure control. As described above, analog signals captured by the image sensor 232A are converted to digital signals (endoscopic image) by the A/D conversion unit 233A. In FIGS. 2 and 3, the output value from the image sensor 232A is shown on the vertical axis. Moreover, the image plane illuminance of the image sensor 232A corresponding to each output value is shown on the horizontal axis. Note that the output value from the image sensor 232A may be a mean value of output values corresponding to each pixel.

Moreover, with reference to FIG. 2A, an appropriate value of the output value from the image sensor 232A is shown as "U0A", and the image plane illuminance of the image sensor 232A corresponding to the appropriate value U0A is shown as "L0A". As shown in FIG. 2, for example, it is assumed that the output value U1A from the image sensor 232A is larger than the appropriate value U0A. In such a case, the automatic exposure control unit 110A performs exposure control so as to decrease the output value from the image sensor 232A by dU1A (U1A−U0A=dU1A).

On the other hand, with reference to FIG. 3, as in FIG. 2, the appropriate value of the output value from the image sensor 232 is shown as "U0A", and the image plane illuminance of the image sensor 232A corresponding to the appropriate value U0A is shown as "L0A". As shown in FIG. 3, for example, it is assumed that the output value U2A from the image sensor 232A is smaller than the appropriate value U0A. In such a case, the automatic exposure control unit 110A performs exposure control so as to increase the output value from the image sensor 232A by dU2A (U0A−U2A=dU2A).

For example, the exposure control may be performed by adjusting parameters for controlling exposure. A variety of parameters are assumed as the parameter for controlling exposure. For example, the parameter for controlling exposure may include at least any one of an electronic shutter speed of the image sensor 232A and a gain by which the analog signals captured by the image sensor 232A are multiplied. Alternatively, the parameter for controlling exposure may include brightness of the white light source 310A.

For example, the exposure control to decrease the output value from the image sensor 232A by dU1A as shown in FIG. 2 may be executed by increasing the electronic shutter speed by an amount corresponding to dU1A, or may be executed by decreasing a gain by which the analog signals captured by the image sensor 232A are multiplied by an amount corresponding to dU1A. Alternatively, the exposure control to decrease the output value from the image sensor 232A may be executed by weakening the brightness of the white light source 310A by an amount corresponding to dU1A.

On the other hand, the exposure control to increase the output value from the image sensor 232A by dU2A as shown in FIG. 3 may be executed by decreasing the electronic shutter speed by an amount corresponding to dU2A, or may be executed by increasing a gain by which the analog signals captured by the image sensor 232A are multiplied by an amount corresponding to dU2A. Alternatively, the exposure control to increase the output value from the image sensor 232A may be executed by increasing the brightness of the white light source 310A by an amount corresponding to dU2A.

The specific examples of the exposure control by the automatic exposure control unit 110A have been described above.

1.3. Functional Detail of Automatic Exposure Control Unit

Figure 4:
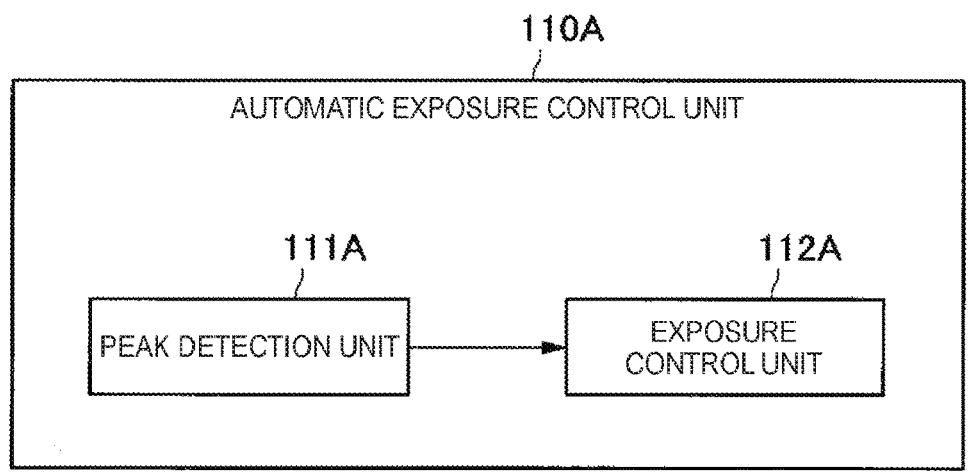
FIG. 4 is a block diagram showing an exemplary detailed functional configuration of an automatic exposure control unit.

Subsequently, detailed function of the automatic exposure control unit 110A will be described. FIG. 4 is a block diagram showing an exemplary detailed functional configuration of the automatic exposure control unit 110A. As shown in FIG. 4, the automatic exposure control unit 110A includes a peak detection unit 111A and an exposure control unit 112A. Hereinafter, each function of the peak detection unit 111A and the exposure control unit 112A will be described in detail. First, the peak detection unit 111A acquires an endoscopic image from the imaging unit 230A.

Figure 5:
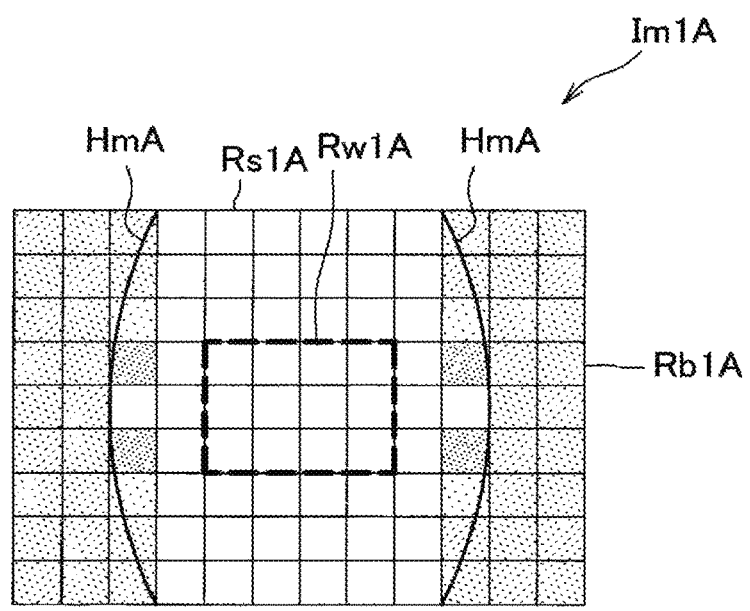
FIG. 5 is a diagram showing an exemplary endoscopic image.

FIG. 5 is a diagram showing an exemplary endoscopic image. As shown in FIG. 5, in an endoscopic image Im1A, each pixel is arranged in a lattice shape. Here, as mentioned above, in the case that an object with higher luminance than inside of a human body (e.g., forceps, gauze or the like) is reflected as a subject, a phenomenon may occur in which the endoscopic image Im1A is partially brightened. In particular, the endoscopic image Im1A is generally captured in a situation that the light source unit 300A and the image sensor 232A are close to each other, and in a situation that the light source unit 300A and the subject are close to each other, so that such a phenomenon is likely to occur. Therefore, there is a white area Rw1A. The color density of each pixel represents the height of the luminance of each pixel.

Here, there is a case where, due to the occurrence of the white area Rw1A in the endoscopic image Im1A, exposure control may be performed by the automatic exposure control unit 110A so that the luminance of the endoscopic image Im1A becomes excessively low. Thus, the observation area Rs1A may become excessively dark. Accordingly, a technology will be described below which is capable of further appropriately adjusting the luminance of the endoscopic image Im1A by reducing the possibility that the observation area Rs1A becomes excessively dark.

Figure 6:
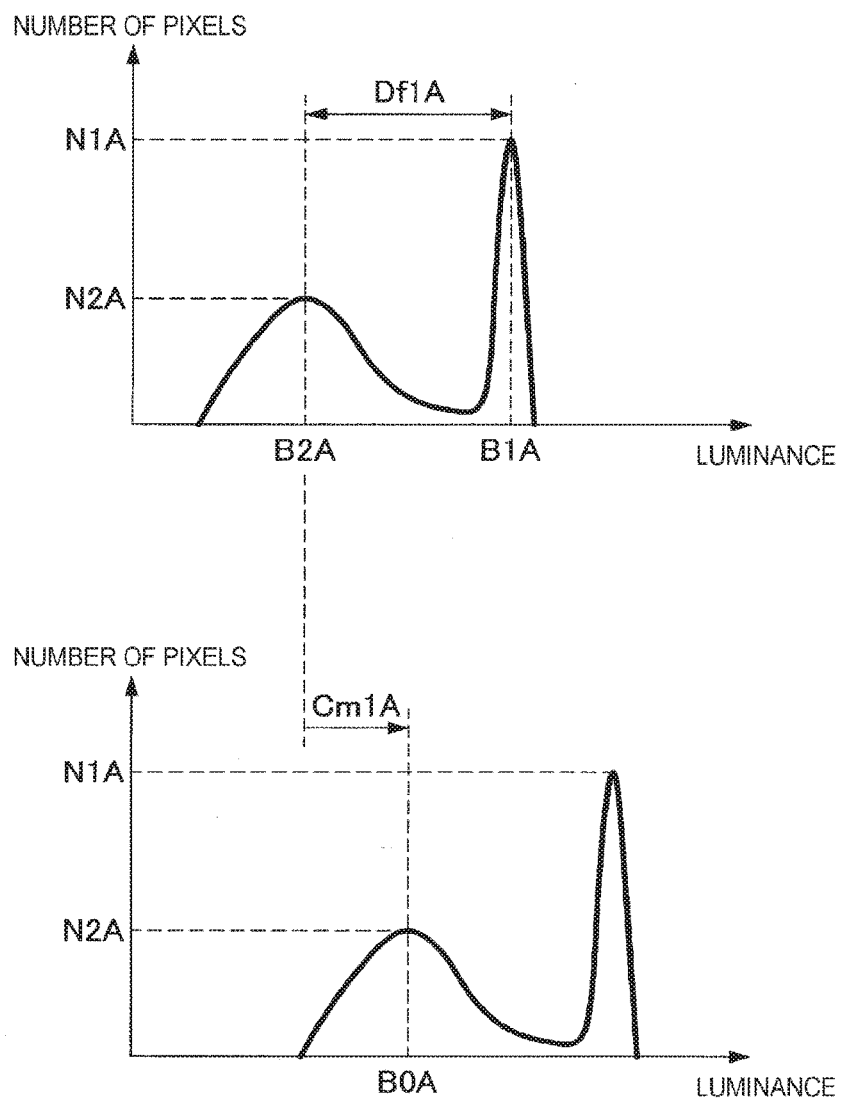
FIG. 6 contains graphs showing an exemplary number-of-pixel distribution for each luminance of an endoscopic image.

Specifically, in the embodiment of the present disclosure, a number-of-pixel distribution for each luminance of the endoscopic image is used. FIG. 6 contains graphs showing an exemplary number-of-pixel distribution for each luminance of the endoscopic image. With reference to FIG. 6, the luminance of the endoscopic image is shown on the horizontal axis, and the number of pixels for each luminance is shown on the vertical axis. Moreover, a first peak (hereinafter, also referred to as "peak B1A") and a second peak (hereinafter, also referred to as "peak B2A") are disposed in sequence from the high luminance side. The numbers of pixels at the peak B1A and the peak B2A are shown as "N1A" and "N2A", respectively.

First, the peak detection unit 111A detects the peak B1A and the peak B2A in sequence from the high luminance side from the number-of-pixel distribution for each luminance of the endoscopic image. Then, in the case that the peak B1A belongs to the white area Rw1A, and the peak B2A belongs to the observation area Rs1A, it is assumed that the darkness of the white area Rw1A changes depending on the luminance difference (first luminance difference) Df1A between the peak B1A and the peak B2A. Accordingly, the exposure control unit 112 may perform exposure control on the basis of the luminance difference Df1A between the peak B1A and the peak B2A. That makes it possible to further appropriately adjust the luminance of the endoscopic image Im1A by reducing a possibility that the observation area Rs1A becomes excessively dark.

For example, the exposure control unit 112A may acquire a correction value of the parameter (hereinafter, also referred to as "first correction value") on the basis of the luminance difference Df1A, correct the parameter on the basis of the first correction value, and perform exposure control on the basis of the corrected parameter. The exposure control unit 112A may correct the parameter by adding the first correction value to the parameter. In FIG. 6, an example is shown in which the peak B2A moves to the position of the peak B0A as a result of the exposure control performed on the basis of the corrected parameter (the example is shown in which the position of the peak B2A has moved by "Cm1A").

The method of acquiring the first correction value is not limited in particular. For example, the exposure control unit 112A may acquire the first correction value corresponding to the luminance difference Df1A from a table, or may acquire the first correction value by calculation on the basis of the luminance difference Df1A. The method of acquiring the first correction value by calculation on the basis of the luminance difference Df1A is also not limited in particular. For example, the exposure control unit 112A may calculate the first correction value from the luminance difference Df1A by assuming that the first correction value linearly changes with respect to the luminance difference Df1A.

Moreover, the exposure control unit 112A may correct the parameter in the case that the luminance difference Df1A is greater than a threshold (hereinafter, also referred to as "first threshold"), while not correcting the parameter in the case that the luminance difference Df1A is less than the first threshold. This is because in the case that the luminance difference Df1A is less than the first threshold, the exposure control is less likely to be performed so that the luminance of the endoscopic image Im1A is excessively lower. Note that, in the case that the luminance difference Df1A is equal to the first threshold, the parameter may be corrected or may not be corrected.

Note that the exposure control unit 112A may correct the parameter in the case that the number of pixels of the peak B1A exceeds the predetermined number of pixels, while not correcting the parameter in the case that the number of pixels of the peak B1A does not exceed the predetermined number of pixels. This is because in the case that the number of pixels of the peak B1A does not exceed the predetermined number of pixels, the exposure control is less likely to be performed so that the luminance of the endoscopic image Im1A is excessively lower. Note that the number of pixels of the peak B1A is equal to the predetermined number of pixels, the parameter may be corrected or may not be corrected.

Figure 7:
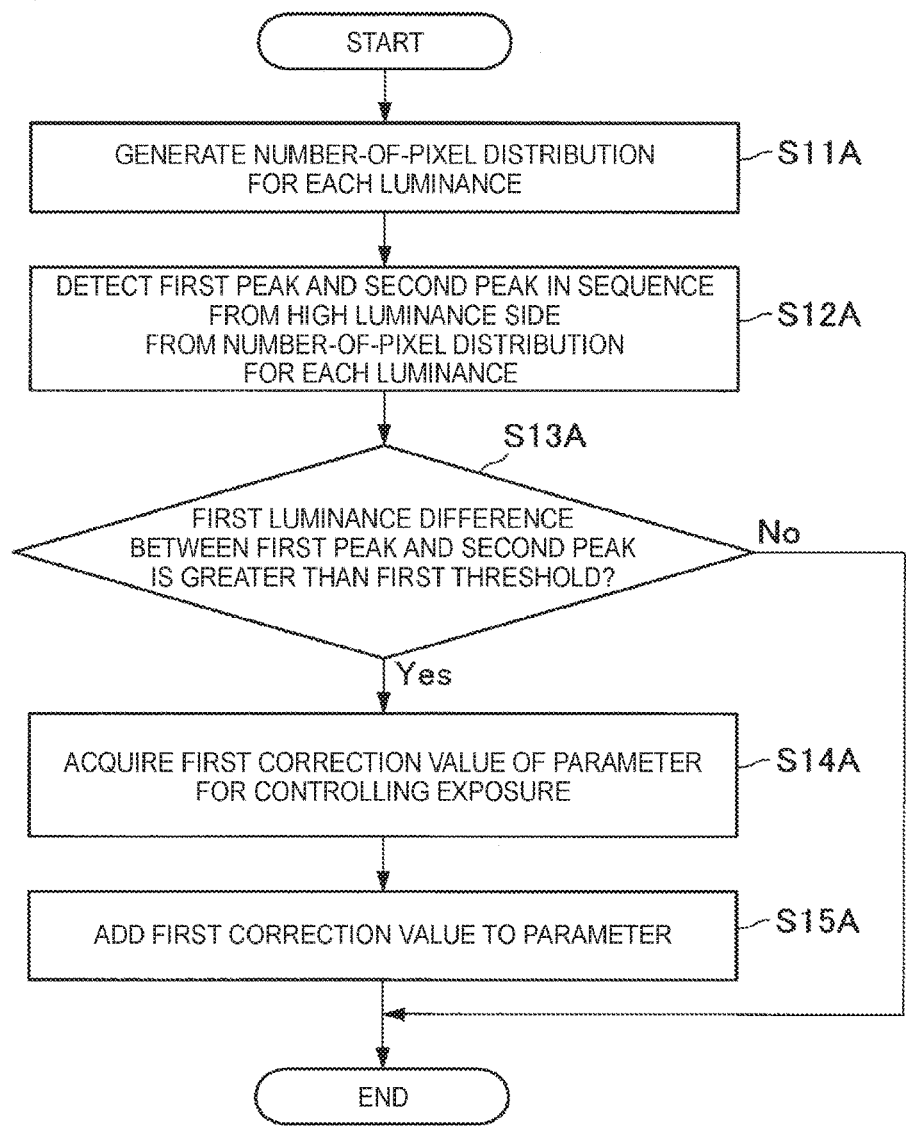
FIG. 7 is a flowchart showing an exemplary operation in a case of detecting two peaks from the high luminance side.

Subsequently, an exemplary operation of the peak detection unit 111A and the exposure control unit 112A as described above will be described. FIG. 7 is a flowchart showing an exemplary operation in the case of detecting two peaks (peak B1A and peak B2A) from the low luminance side. Note that the exemplary operation shown in FIG. 7 is merely an example of operation of the peak detection unit 111A and the exposure control unit 112A. Accordingly, the operation of the peak detection unit 111A and the exposure control unit 112A is not limited to the exemplary operation shown in FIG. 7.

First, as shown in FIG. 7, the peak detection unit 111A generates a number-of-pixel distribution for each luminance in the endoscopic image (S11A). Then, the peak detection unit 111 detects a first peak (peak B1A) and a second peak (peak B2A) in sequence from the high luminance side from the number-of-pixel distribution for each luminance (S12A). Subsequently, in the case that the first luminance difference (luminance difference Df1A) between the first peak (peak B1A) and the second peak (peak B2A) is less than the first threshold ("No" in S13A), the exposure control unit 112A ends the operation.

On the other hand, in the case that the first luminance difference (luminance difference Df1A) between the first peak (peak B1A) and the second peak (peak B2A) is greater than the first threshold ("Yes" in S13A), the exposure control unit 112A acquires a first correction value of the parameter for controlling exposure (S14A), adds the first correction value to the parameter (S15A), and ends the operation. If the exposure control is performed on the basis of the parameter to which the first correction value has been added, the possibility that the observation area Rs1A becomes excessively dark is reduced, and it is possible to further appropriately adjust the luminance of the endoscopic image Im1A.

The case in which the white area Rw1A is generated in the endoscopic image Im1A has been described above.

Here, a phenomenon may occur in which the endoscopic image Im1A is partially darkened by light shielding caused by, for example, the hood of the lens for transmitting light to the image sensor 232A. Hereinafter, such an area darkened by light shielding in the endoscopic image Im1A is also simply referred to as "black area". Moreover, a phenomenon in which such a black area occurs in the endoscopic image Im1A is also called "vignetting".

Here, there is a case where, due to the occurrence of the black area Rb1A in the endoscopic image Im1A, exposure control may be performed by the automatic exposure control unit 110A so that the luminance of the endoscopic image Im1A becomes excessively high. Thus, the observation area Rs1A may become excessively bright. Accordingly, a technology will be described below which is capable of further appropriately adjusting the luminance of the endoscopic image Im1A by reducing the possibility that the observation area Rs1A becomes excessively bright.

Figure 8:
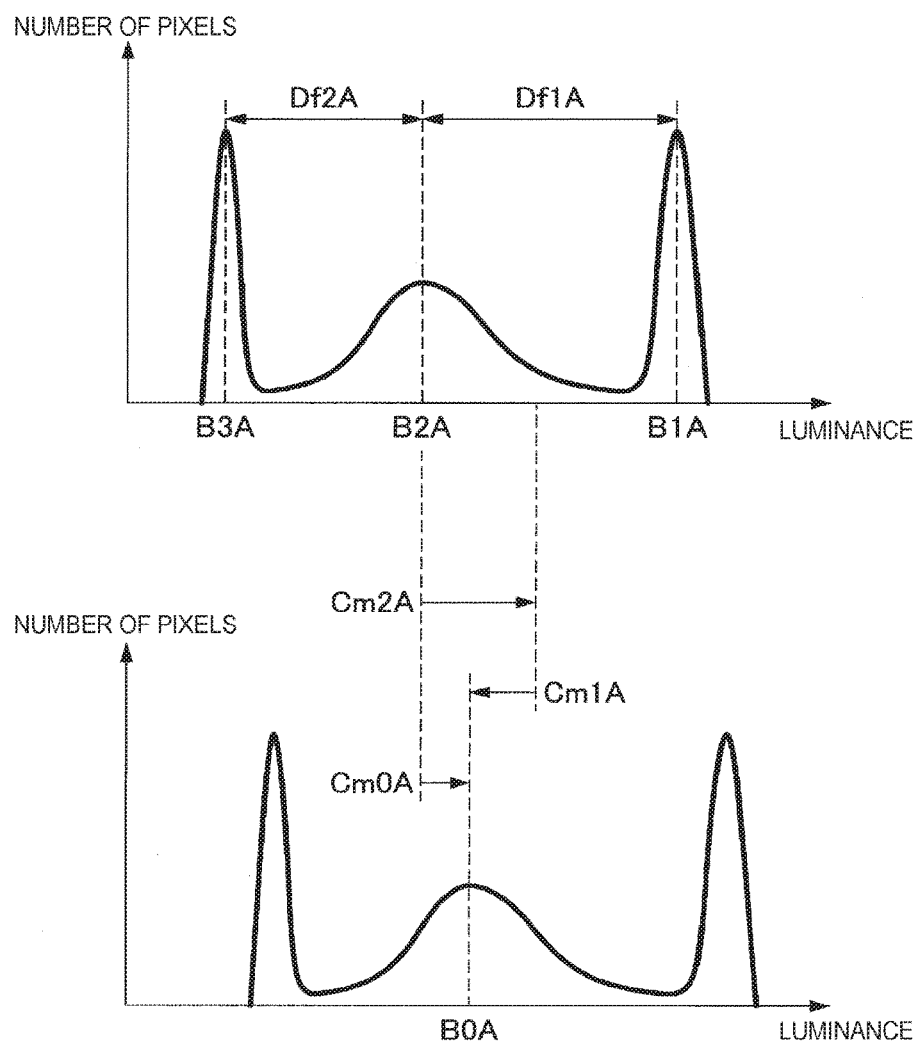
FIG. 8 contains graphs showing another example of a number-of-pixel distribution for each luminance of the endoscopic image.

FIG. 8 contains graphs showing another example of a number-of-pixel distribution for each luminance of the endoscopic image. With reference to FIG. 8, the luminance of the endoscopic image is shown on each horizontal axis, and the number of pixels for each luminance is shown on each vertical axis. Moreover, a first peak (peak B1A) and a second peak (peak B2A) followed by a third peak (hereinafter, also referred to as "peak B3A") are disposed in sequence from the high luminance side. The numbers of pixels at the peak B1A, the peak B2A and the peak B3A are shown as "N1A", "N2A" and "N3A", respectively.

First, the peak detection unit 111A detects the peak B3A on the lower luminance side of the peak B2A from the number-of-pixel distribution for each luminance of the endoscopic image. Then, in the case that the peak B3A belongs to a black area Rb1A, and the peak B2A belongs to the observation area Rs1A, it is assumed that the brightness of the black area Rb1A changes depending on the luminance difference (second luminance difference) Df2A between the peak B3A and the peak B2A. Thus, the exposure control unit 112A may perform exposure control on the basis of the luminance difference Df1A and the luminance difference (second luminance difference) Df2A between the peak B3A and the peak B2A. That makes it possible to further appropriately adjust the luminance of the endoscopic image Im1A by reducing a possibility that the observation area Rs1A becomes excessively bright.

For example, the exposure control unit 112A may acquire a correction value of the parameter (hereinafter, also referred to as "second correction value") on the basis of the luminance difference Df2A, correct the parameter on the basis of the first correction value and the second correction value, and perform exposure control on the basis of the corrected parameter. The exposure control unit 112A may correct the parameter by adding the first correction value and the second correction value to the parameter. In FIG. 8, an example is shown in which the peak B2A moves to the position of the peak B0A as a result of the exposure control performed on the basis of the corrected parameter (the example is shown in which the position of the peak B2A has moved by the sum "Cm0A" of "Cm1A" and "Cm2A").

The method of acquiring the second correction value is not limited in particular. For example, the exposure control unit 112A may acquire the second correction value corresponding to the luminance difference Df2A from a table, or may acquire the second correction value by calculation on the basis of the luminance difference Df2A. The method of acquiring the second correction value by calculation on the basis of the luminance difference Df2A is also not limited in particular. For example, the exposure control unit 112A may calculate the second correction value from the luminance difference Df2A by assuming that the second correction value linearly changes with respect to the luminance difference Df2A.

Moreover, the exposure control unit 112A may correct the parameter in the case that the luminance difference Df2A is greater than a threshold (hereinafter, also referred to as "second threshold"), while not correcting the parameter in the case that the luminance difference Df2A is less than the second threshold. This is because in the case that the luminance difference Df2A is less than the second threshold, the exposure control is less likely to be performed so that the luminance of the endoscopic image Im1A becomes excessively high. Note that in the case that the luminance difference Df2A is equal to the second threshold, the parameter may be corrected or may not be corrected.

Moreover, the exposure control unit 112A may correct the parameter in the case that the number of pixels of the peak B3A exceeds a predetermined number of pixels, while not correcting the parameter in the case that the number of pixels of the peak B3A does not exceed the predetermined number of pixels. This is because in the case that the number of pixels of the peak B3A does not exceed the predetermined number of pixels, the exposure control is less likely to be performed so that the luminance of the endoscopic image Im1A becomes excessively high. Note that in the case that the number of pixels of the peak B3A is equal to the predetermined number of pixels, the parameter may be corrected or may not be corrected.

Figure 9:
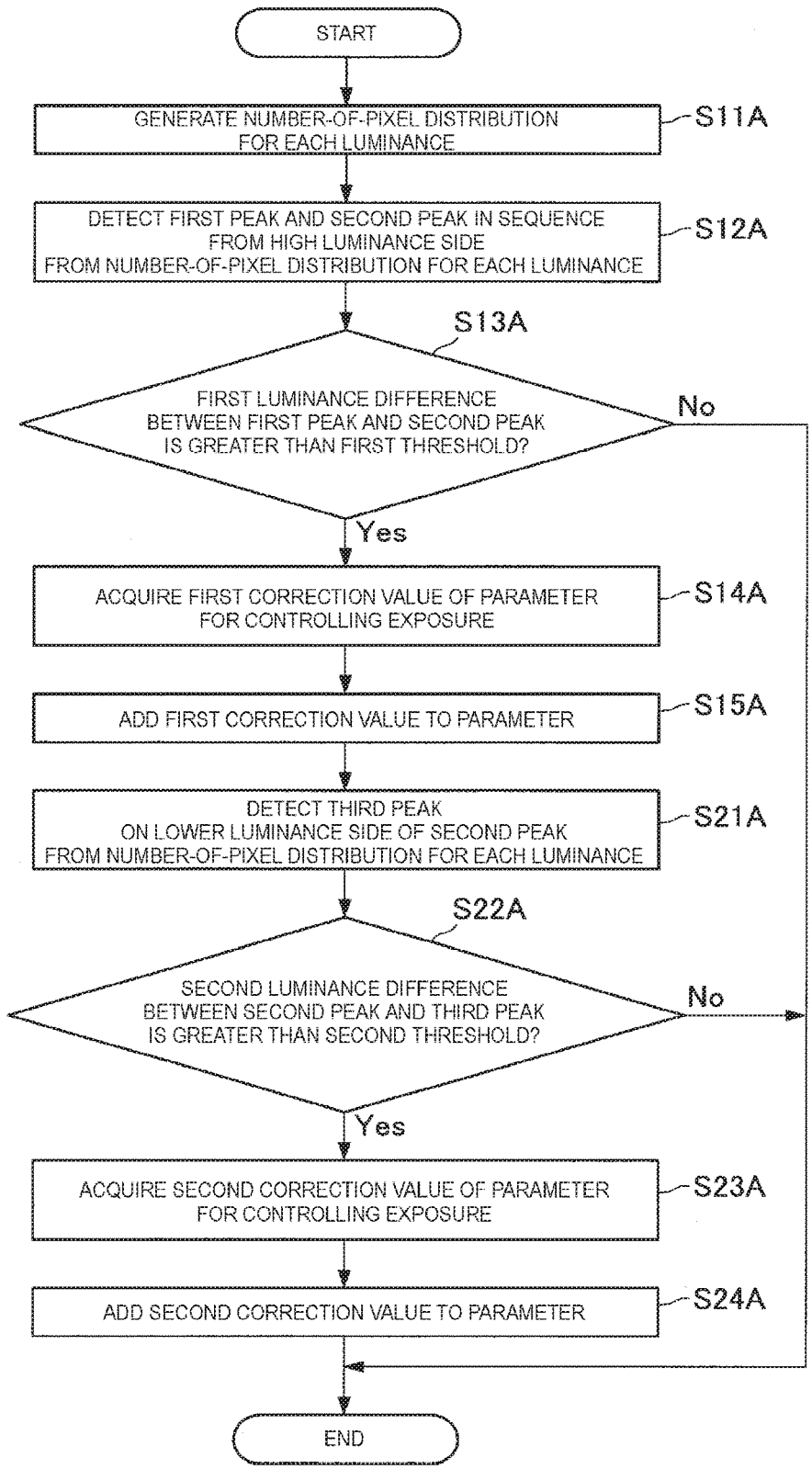
FIG. 9 is a flowchart showing an exemplary operation in a case of detecting three peaks from the high luminance side.

Subsequently, an exemplary operation of the peak detection unit 111A and the exposure control unit 112A as described above will be described. FIG. 9 is a flowchart showing an exemplary operation in the case of detecting three peaks (peak B1A, peak B2A and peak B3A) from the low luminance side. Note that the exemplary operation shown in FIG. 9 is merely an example of operation of the peak detection unit 111A and the exposure control unit 112A. Accordingly, the operation of the peak detection unit 111A and the exposure control unit 112A is not limited to the exemplary operation shown in FIG. 9.

S11A to S15A shown in FIG. 9 are executed as with S11A to S15A shown in FIG. 7. Subsequent to S15A, the peak detection unit 111A detects the third peak (peak B3A) on the lower luminance side of the second peak (peak B2A from a number-of-pixel distribution for each luminance (S21A). Subsequently, in the case that the second luminance difference (luminance difference Df2A) between the third peak (peak B3A) and the second peak (peak B2A) is less than the second threshold ("No" in S22A), the exposure control unit 112A ends the operation.

On the other hand, in the case that the second luminance difference (luminance difference Df2A) between the third peak (peak B3A) and the second peak (peak B2A) is greater than the second threshold ("Yes" in S22A), the exposure control unit 112A acquires the second correction value of the parameter for controlling exposure (S23A), adds the second correction value to the parameter (S24A), and ends the operation. If the exposure control is performed on the basis of the parameter to which the second correction value has been added, the possibility that the observation area Rs1A becomes excessively bright is reduced, and it is possible to further appropriately adjust the luminance of the endoscopic image Im1A.

The case in which the black area Rb1A is generated in the endoscopic image Im1A has been described above. Moreover, the detailed function of the automatic exposure control unit 110A has been described.

2. CONCLUSION

As described above, according to the embodiment of the present disclosure, the image processing device 100A is provided which includes the peak detection unit 111A configured to detect the first peak (peak B1A) and the second peak (peak B2A) in sequence from the high luminance side from the number-of-pixel distribution for each luminance of the endoscopic image Im1A based on imaging by the image sensor 232A, and the exposure control unit 112A configured to perform exposure control on the basis of the luminance difference Df1A between the first peak and the second peak. According to such a configuration, it is possible to further appropriately adjust the luminance of the endoscopic image Im1A by reducing the possibility that the observation area Rs1A becomes excessively dark.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An image processing device including:

a peak detection unit configured to detect a first peak and a second peak in sequence from a high luminance side from a number-of-pixel distribution for each luminance of an endoscopic image based on imaging by an image sensor; and an exposure control unit configured to perform exposure control on a basis of a first luminance difference between the first peak and the second peak.

(2)

The image processing device according to (1), in which the exposure control unit performs the exposure control by acquiring a first correction value of a parameter for controlling exposure on a basis of the first luminance difference, and correcting the parameter on a basis of the first correction value.

(3)

The image processing device according to (2), in which the exposure control unit corrects the parameter by adding the first correction value to the parameter.

(4)

The image processing device according to (2) or (3), in which the exposure control unit acquires the first correction value corresponding to the first luminance difference from a table.

(5)

The image processing device according to (2) or (3), in which the exposure control unit acquires the first correction value by calculation on a basis of the first luminance difference.

(6)

The image processing device according to (5), in which the exposure control unit calculates the first correction value from the first luminance difference by assuming that the first correction value linearly changes with respect to the first luminance difference.

(7)

The image processing device according to any one of (1) to (6), in which the exposure control unit performs the exposure control in a case that the first luminance difference is greater than a threshold.

(8)

The image processing device according to any one of (1) to (7), in which the exposure control unit performs the exposure control in a case that the number of pixels of the first peak exceeds a predetermined number of pixels.

(9)

The image processing device according to any one of (2) to (6), in which the peak detection unit detects a third peak on a lower luminance side of the second peak, and the exposure control unit performs the exposure control on a basis of the first luminance difference and a second luminance difference between the second peak and the third peak.

(10)

The image processing device according to (9), in which the exposure control unit performs the exposure control by acquiring a second correction value of the parameter on a basis of the second luminance difference, and correcting the parameter on a basis of the first correction value and the second correction value.

(11)

The image processing device according to (10), in which the exposure control unit corrects the parameter by adding the first correction value and the second correction value to the parameter.

(12)

The image processing device according to any one of (2) to (6), in which the parameter includes at least any one of an electronic shutter speed of the image sensor and a gain by which an analog signal captured by the image sensor is multiplied.

(13)

The image processing device according to any one of (2) to (6), in which the parameter includes brightness of a light source.

(14)

An image processing method including:

detecting a first peak and a second peak in sequence from a high luminance side from a number-of-pixel distribution for each luminance of an endoscopic image based on imaging by an image sensor; and performing exposure control by a processor on a basis of a first luminance difference between the first peak and the second peak.

(15)

A program for causing a computer to function as an image processing device including:

a peak detection unit configured to detect a first peak and a second peak in sequence from a high luminance side from a number-of-pixel distribution for each luminance of an endoscopic image based on imaging by an image sensor; and an exposure control unit configured to perform exposure control on a basis of a first luminance difference between the first peak and the second peak.

(16)

An image processing system including:

a light source unit configured to emit light;

an image sensor configured to capture an endoscopic image by receiving reflected light of the light emitted by the light source unit; and an image processing device including a peak detection unit configured to detect a first peak and a second peak in sequence from a high luminance side from a number-of-pixel distribution for each luminance of the endoscopic image, and an exposure control unit configured to perform exposure control on a basis of a first luminance difference between the first peak and the second peak.

Subsequently, another embodiment will be described. Description will be given in the following order.

3. Background
4. Embodiment of the Present Disclosure
   4.1. Exemplary system configuration
   4.2. Exemplary function configuration
   4.3. Functional detail of automatic exposure control unit
5. Conclusion

3. BACKGROUND

In recent years, image processing devices for processing an endoscopic image based on imaging by an image sensor have gained in popularity (e.g., see JP 2013-42998A). Meanwhile, a phenomenon may occur in which the endoscopic image is partially darkened by light shielding caused by, for example, the hood of the lens for transmitting light to the image sensor. Hereinafter, such an area darkened by light shielding in the endoscopic image is also simply referred to as "black area". Moreover, a phenomenon in which such a black area occurs in the endoscopic image is also called "vignetting".

Here, due to the occurrence of the black area in the endoscopic image, there is a case where exposure control may be performed so that the luminance of the endoscopic image becomes excessively high. Thus, an area other than the black area (hereinafter, also referred to as "observation area") may become excessively bright. Accordingly, it is desirable to provide a technology capable of further appropriately adjusting the luminance of the endoscopic image.

According to the present disclosure, there is provided an image processing device including: a peak detection unit configured to detect a first peak and a second peak in sequence from a low luminance side from a number-of-pixel distribution for each luminance of an endoscopic image based on imaging by an image sensor; and an exposure control unit configured to perform exposure control on a basis of a first luminance difference between the first peak and the second peak.

According to the present disclosure, there is provided an image processing method including: detecting a first peak and a second peak in sequence from a low luminance side from a number-of-pixel distribution for each luminance of an endoscopic image based on imaging by an image sensor; and performing exposure control by a processor on a basis of a first luminance difference between the first peak and the second peak.

According to the present disclosure, there is provided a program for causing a computer to function as an image processing device including: a peak detection unit configured to detect a first peak and a second peak in sequence from a low luminance side from a number-of-pixel distribution for each luminance of an endoscopic image based on imaging by an image sensor; and an exposure control unit configured to perform exposure control on a basis of a first luminance difference between the first peak and the second peak.

According to the present disclosure, there is provided an image processing system including: a light source unit configured to emit light; an image sensor configured to capture an endoscopic image by receiving reflected light of the light emitted by the light source unit; and an image processing device including a peak detection unit configured to detect a first peak and a second peak in sequence from a low luminance side from a number-of-pixel distribution for each luminance of the endoscopic image, and an exposure control unit configured to perform exposure control on a basis of a first luminance difference between the first peak and the second peak.

As described above, according to the present disclosure, a technology capable of further appropriately adjusting luminance of an endoscopic image is provided. Note that the effects described above are not necessarily limitative. With or in the place of the above effects, there may be achieved any one of the effects described in this specification or other effects that may be grasped from this specification.

4. EMBODIMENT OF THE PRESENT DISCLOSURE

4.1. Exemplary System Configuration

Figure 10:
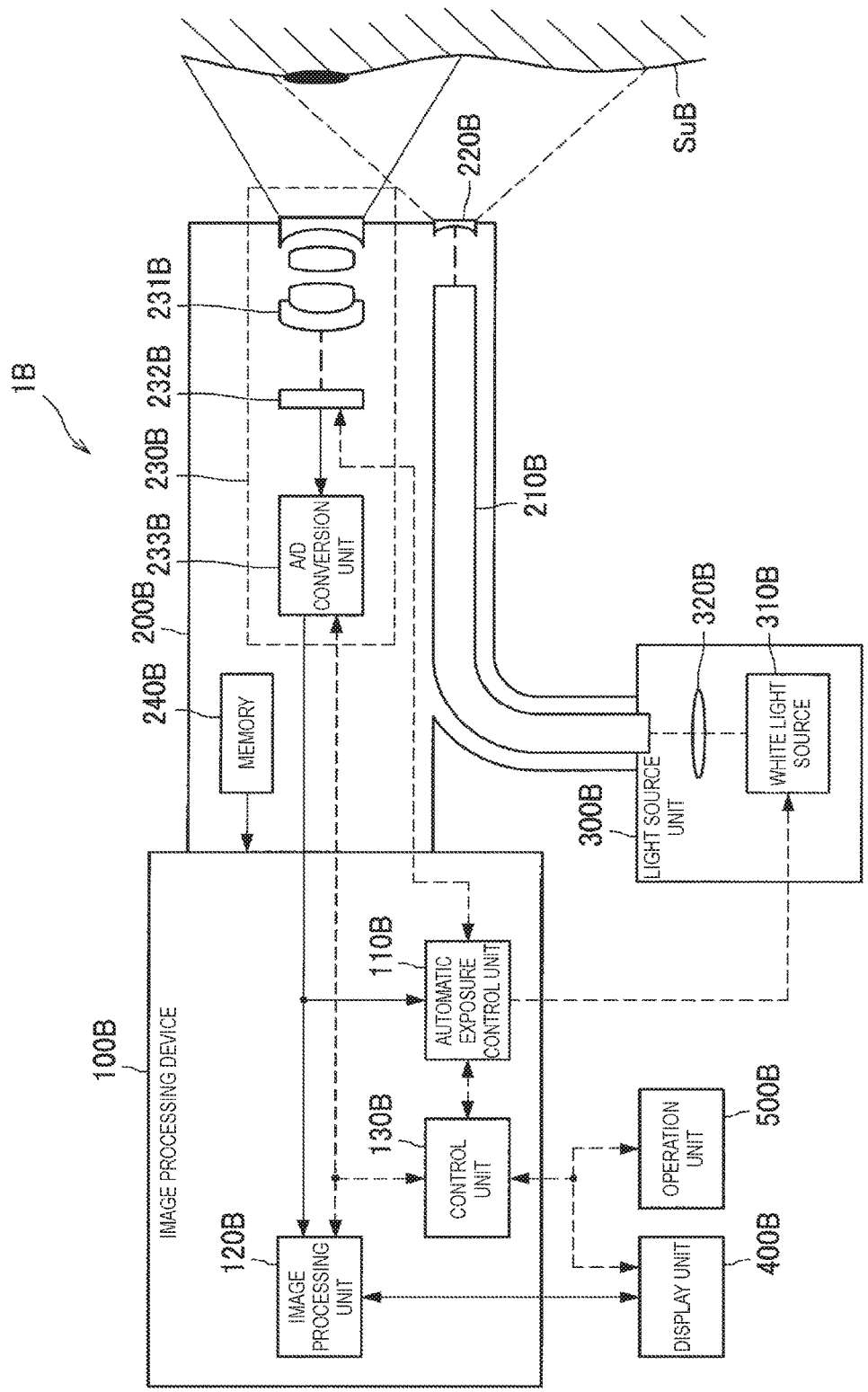
FIG. 10 is a diagram showing an exemplary configuration of the image processing system according to an embodiment of the present disclosure.

First, an exemplary configuration of an image processing system according to an embodiment of the present disclosure will be described with reference to the drawings. FIG. 10 is a diagram showing an exemplary configuration of an image processing system according to an embodiment of the present disclosure. As shown in FIG. 10, the image processing system 1B includes an image processing device 100B, an insertion unit 200B, a light source unit 300B, a display unit 400B, and an operation unit 500B.

The light source unit 300B includes a white light source 310B and a condenser lens 320B. The white light source 310B emits white light. Note that this specification mainly describes examples of using white light, but the color of light is not limited in particular. Accordingly, instead of the white light source 310B, light sources which emit visible light other than white may be used. The condenser lens 320B focuses the light emitted by the white light source 310B to a light guide 210B described below.

The insertion unit 200B can correspond to a scope to be inserted into a body. Specifically, the insertion unit 200B may be a rigid endoscope or a soft endoscope. The insertion unit 200B includes the light guide 210B, an illumination lens 220B, an imaging unit 230B, and a memory 240B. The imaging unit 230B includes an objective lens 231B, an image sensor (imaging element) 232B, and an A/D (analog/digital) conversion unit 233B.

The light guide 210B guides the light focused by the light source unit 300B to the end of the insertion unit 200B. The illumination lens 220B diffuses the light that has been guided to the end by the light guide 210B, and irradiates an observation target (subject SuB) with the diffused light. The objective lens 231B focuses the reflected light returning from the observation target (subject SuB) to form an image on the image sensor 232B. The image sensor 232B outputs analog signals (endoscopic image) captured by receiving the reflected light to the A/D conversion unit 233B.

Note that the image sensor 232B has, for example, a primary color Bayer array. In such a case, the endoscopic image obtained by the image sensor 232B is a primary color Bayer image. The primary color Bayer image is an image in which each pixel has any of R, G, and B signals, and the RGB pixels are arranged in a staggered pattern. However, the image sensor 232B is not limited to the primary color Bayer array. Namely, the endoscopic image is not limited to the primary color Bayer image. For example, the endoscopic image may be an image acquired by an endoscope imaging method e.g., complementary-color method or frame-sequential imaging method other than the primary color Bayer.

The A/D conversion unit 233B converts, on the basis of a control signal output from a control unit 130B described below, analog signals (endoscopic image) output from the image sensor 232B into digital signals, and outputs the digital signals (endoscopic image) to the image processing device 100B. The memory 240B stores a program for implementing function of the image processing device 100B when being executed by an operation device (not shown).

Note that in the following description, the insertion unit 200B may be referred to as "scope" as appropriate. A different scope can be used for endoscopic diagnosis depending on a diagnosis region. An identification number for specifying a target diagnosis region and a function, such as a zoom function, is assigned to each scope, and in this specification, the identification number may be referred to as "scope ID". The memory 240B stores the scope ID.

The image processing device 100B includes an automatic exposure control unit 110B, an image processing unit 120B, and the control unit 130B. The endoscopic image acquired by the imaging unit 230B is output to the automatic exposure control unit 110B and the image processing unit 120B. The automatic exposure control unit 110B is connected to the white light source 310B and the image sensor 232B, and controls the white light source 310B and the image sensor 232B. The image processing unit 120B is connected to the display unit 400B. The control unit 130B is bidirectionally connected to the imaging unit 230B, the image processing unit 120B, the display unit 400B, and the operation unit 500B, and controls these components.

The automatic exposure control unit 110B automatically performs exposure control of the image sensor 232B such that the luminance of the endoscopic image acquired by the imaging unit 230B is a value appropriate for observation (hereinafter, referred to as "appropriate value"). The automatic exposure control unit 110B will be described in detail below. The image processing unit 120B performs image processing on the endoscopic image captured by the imaging unit 230B. The image processing unit 120B performs, for example, a tone transformation process and a noise reduction process. The image processing unit 120B outputs the image subjected to the image processing to the display unit 400B.

The control unit 130B is connected to the imaging unit 230B, the image processing unit 120B, the display unit 400B, and the operation unit 500B, and outputs control signals for controlling these. The display unit 400B outputs the endoscopic image output by the image processing unit 120B to an image display device such as an endoscope monitor. The operation unit 500B is an interface for receiving operations from a user. For example, the operation unit 500B includes a power switch for turning ON/OFF the power supply, a shutter button for starting an imaging operation, a mode switch button for switching an imaging mode and other various modes, and the like.

The exemplary configuration of the image processing system 1B according to the embodiment of the present disclosure has been described above.

4.2. Example of Exposure Control

Figure 11:
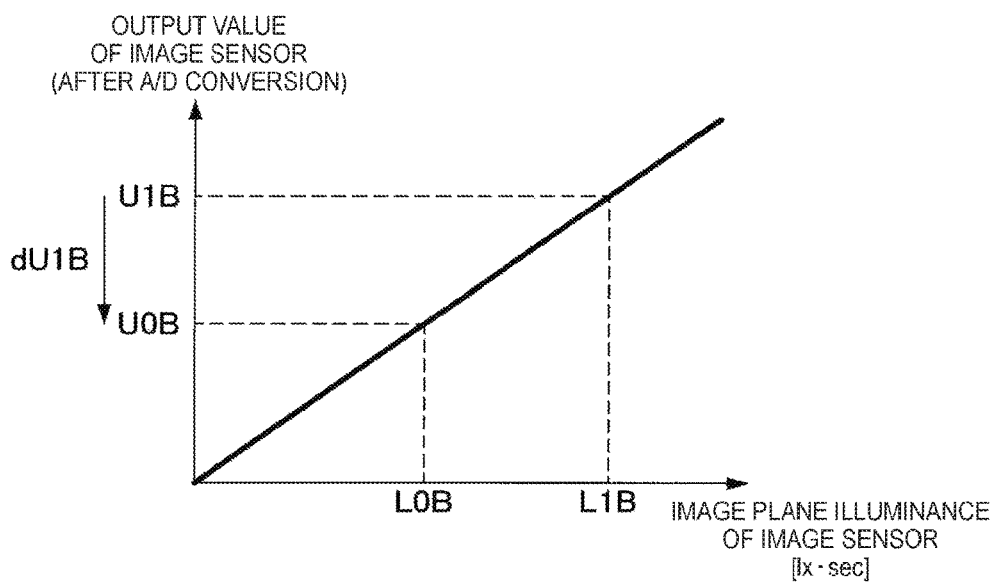
FIG. 11 is an explanatory graph of a specific example of exposure control.
Figure 12:
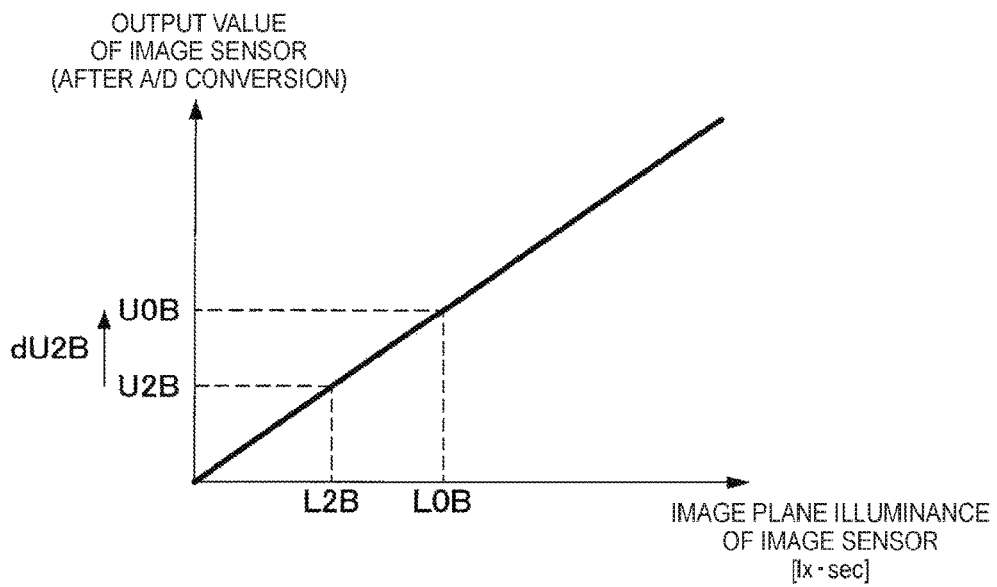
FIG. 12 is an explanatory graph of a specific example of exposure control.

Subsequently, specific examples of exposure control by the automatic exposure control unit 110B will be described. FIGS. 11 and 12 are explanatory graphs of specific examples of the exposure control. As described above, analog signals captured by the image sensor 232B are converted to digital signals (endoscopic image) by the A/D conversion unit 233B. In FIGS. 11 and 12, the output value from the image sensor 232B is shown on the vertical axis. Moreover, the image plane illuminance of the image sensor 232B corresponding to each output value is shown on the horizontal axis. Note that the output value from the image sensor 232B may be a mean value of output values corresponding to each pixel.

Moreover, with reference to FIG. 11, an appropriate value of the output value from the image sensor 232B is shown as "U0B", and the image plane illuminance of the image sensor 232B corresponding to the appropriate value U0B is shown as "L0B". As shown in FIG. 11, for example, it is assumed that the output value U1B from the image sensor 232B is larger than the appropriate value U0B. In such a case, the automatic exposure control unit 110B performs exposure control so as to decrease the output value from the image sensor 232B by dU1B (U1B−U0B=dU1B).

On the other hand, with reference to FIG. 12, as in FIG. 11, the appropriate value of the output value from the image sensor 232B is shown as "U0B", and the image plane illuminance of the image sensor 232B corresponding to the appropriate value U0B is shown as "L0B". As shown in FIG. 12, for example, it is assumed that the output value U2B from the image sensor 232B is smaller than the appropriate value U0B. In such a case, the automatic exposure control unit 110B performs exposure control so as to increase the output value from the image sensor 232B by dU2B (U0B−U2B=dU2B).

For example, the exposure control may be performed by adjusting parameters for controlling exposure. A variety of parameters are assumed as the parameter for controlling exposure. For example, the parameter for controlling exposure may include at least any one of an electronic shutter speed of the image sensor 232B and a gain by which the analog signals captured by the image sensor 232B are multiplied. Alternatively, the parameter for controlling exposure may include brightness of the white light source 310B.

For example, the exposure control to decrease the output value from the image sensor 232B by dU1B as shown in FIG. 11 may be executed by increasing the electronic shutter speed by an amount corresponding to dU1B, or may be executed by decreasing a gain by which the analog signals captured by the image sensor 232B are multiplied by an amount corresponding to dU1B. Alternatively, the exposure control to decrease the output value from the image sensor 232B may be executed by weakening the brightness of the white light source 310B by an amount corresponding to dU1B.

On the other hand, the exposure control to increase the output value from the image sensor 232B by dU2B as shown in FIG. 12 may be executed by decreasing the electronic shutter speed by an amount corresponding to dU2B, or may be executed by increasing a gain by which the analog signals captured by the image sensor 232B are multiplied by an amount corresponding to dU2B. Alternatively, the exposure control to increase the output value from the image sensor 232B may be executed by increasing the brightness of the white light source 310B by an amount corresponding to dU2B.

The specific examples of the exposure control by the automatic exposure control unit 110B have been described above.

4.3. Functional Detail of Automatic Exposure Control Unit

Figure 13:
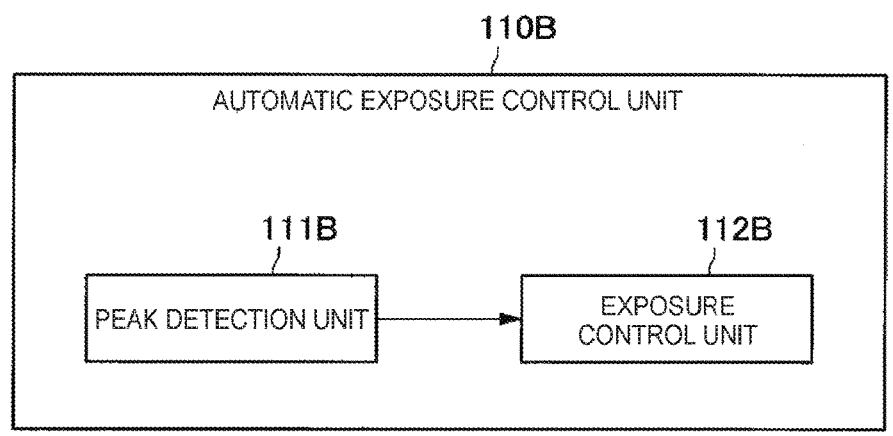
FIG. 13 is a block diagram showing an exemplary detailed functional configuration of an automatic exposure control unit.

Subsequently, detailed function of the automatic exposure control unit 110 will be described. FIG. 13 is a block diagram showing an exemplary detailed functional configuration of the automatic exposure control unit 110B. As shown in FIG. 13, the automatic exposure control unit 110B includes a peak detection unit 111B and an exposure control unit 112B. Hereinafter, each function of the peak detection unit 111B and the exposure control unit 112B will be described in detail. First, the peak detection unit 111B acquires an endoscopic image from the imaging unit 230B.

Figure 14:
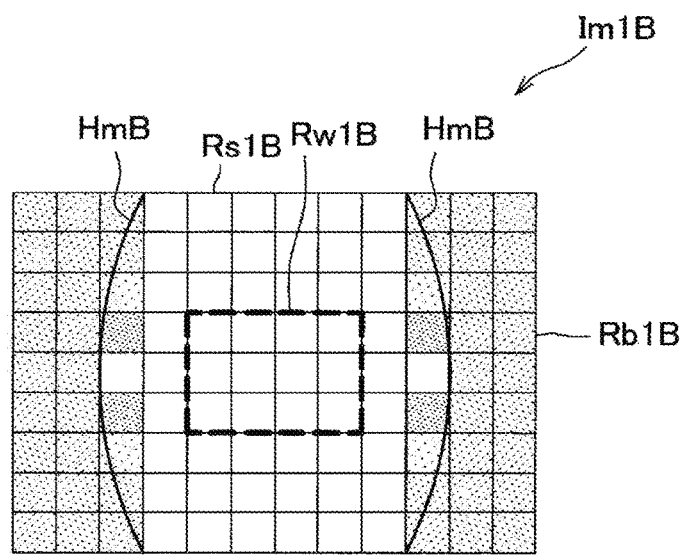
FIG. 14 is a diagram showing an exemplary endoscopic image.

FIG. 14 is a diagram showing an exemplary endoscopic image. As shown in FIG. 14, in an endoscopic image Im1B, each pixel is arranged in a lattice shape. Here, as mentioned above, a phenomenon may occur in which the endoscopic image Im1B is partially darkened by light shielding caused by, for example, the hood of the lens for transmitting light to the image sensor 232B. Therefore, in the endoscopic image Im1B, there is a black area Rb1B in addition to an observation area Rs1B. Lines HmB indicate boundary lines between the black areas Rb1B and the observation area Rs1B. The color density of each pixel represents the height of the luminance of each pixel.

Here, there is a case where, due to the occurrence of the black area Rb1B in the endoscopic image Im1B, exposure control may be performed by the automatic exposure control unit 110B so that the luminance of the endoscopic image Im1B becomes excessively high. Thus, the observation area Rs1B may become excessively bright. Accordingly, a technology will be described below which is capable of further appropriately adjusting the luminance of the endoscopic image Im1B by reducing the possibility that the observation area Rs1B becomes excessively bright.

Figure 15:
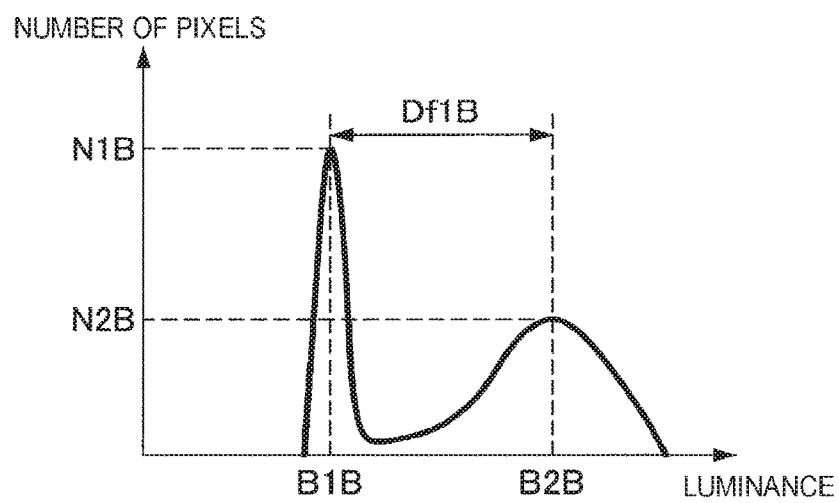
FIG. 15 contains graphs showing an exemplary number-of-pixel distribution for each luminance of the endoscopic image.
Figure 15:
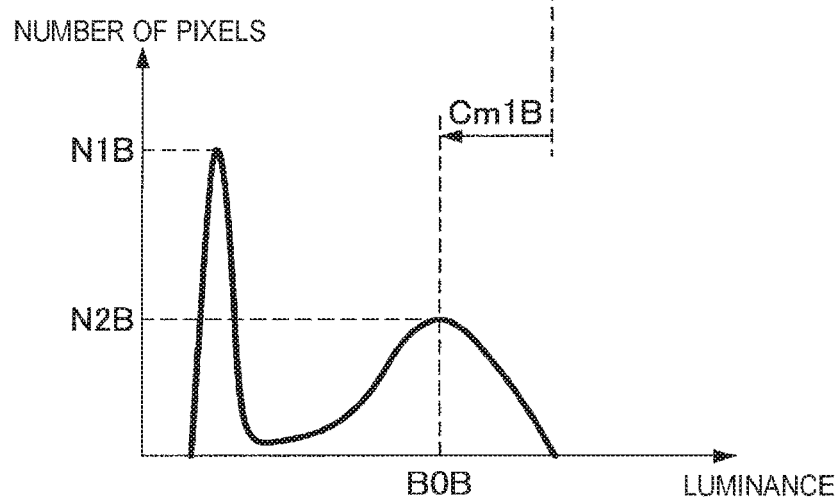

Specifically, in the embodiment of the present disclosure, a number-of-pixel distribution for each luminance of the endoscopic image is used. FIG. 15 contains graphs showing an exemplary number-of-pixel distribution for each luminance of the endoscopic image. With reference to FIG. 15, the luminance of the endoscopic image is shown on the horizontal axis, and the number of pixels for each luminance is shown on the vertical axis. Moreover, a first peak (hereinafter, also referred to as "peak B1B") and a second peak (hereinafter, also referred to as "peak B2B") are disposed in sequence from the low luminance side. The numbers of pixels at the peak B1B and the peak B2B are shown as "N1B" and "N2B", respectively.

First, the peak detection unit 111B detects the peak B1B and the peak B2B in sequence from the low luminance side from the number-of-pixel distribution for each luminance of the endoscopic image. Then, in the case that the peak B1B belongs to the black area Rb1B, and the peak B2B belongs to the observation area Rs1B, it is assumed that the darkness of the black area Rb1B changes depending on the luminance difference (first luminance difference) Df1B between the peak B1B and the peak B2B. Accordingly, the exposure control unit 112B may perform exposure control on the basis of the luminance difference Df1B between the peak B1B and the peak B2B. That makes it possible to further appropriately adjust the luminance of the endoscopic image Im1B by reducing a possibility that the observation area Rs1B becomes excessively bright.

For example, the exposure control unit 112B may acquire a correction value of the parameter (hereinafter, also referred to as "first correction value") on the basis of the luminance difference Df1B, correct the parameter on the basis of the first correction value, and perform exposure control on the basis of the corrected parameter. The exposure control unit 112B may correct the parameter by adding the first correction value to the parameter. In FIG. 15, an example is shown in which the peak B2B moves to the position of the peak B0B as a result of the exposure control performed on the basis of the corrected parameter (the example is shown in which the position of the peak B2B has moved by "Cm1B").

The method of acquiring the first correction value is not limited in particular. For example, the exposure control unit 112B may acquire the first correction value corresponding to the luminance difference Df1B from a table, or may acquire the first correction value by calculation on the basis of the luminance difference Df1B. The method of acquiring the first correction value by calculation on the basis of the luminance difference Df1B is also not limited in particular. For example, the exposure control unit 112B may calculate the first correction value from the luminance difference Df1B by assuming that the first correction value linearly changes with respect to the luminance difference Df1B.

Moreover, the exposure control unit 112B may correct the parameter in the case that the luminance difference Df1B is greater than a threshold (hereinafter, also referred to as "first threshold"), while not correcting the parameter in the case that the luminance difference Df1B is less than the first threshold. This is because in the case that the luminance difference Df1B is less than the first threshold, the exposure control is less likely to be performed so that the luminance of the endoscopic image Im1B is excessively higher. Note that, in the case that the luminance difference Df1B is equal to the first threshold, the parameter may be corrected or may not be corrected.

Note that the exposure control unit 112B may correct the parameter in the case that the number of pixels of the peak B1B exceeds the predetermined number of pixels, while not correcting the parameter in the case that the number of pixels of the peak B1B does not exceed the predetermined number of pixels. This is because in the case that the number of pixels of the peak B1B does not exceed the predetermined number of pixels, the exposure control is less likely to be performed so that the luminance of the endoscopic image Im1B is excessively higher. Note that the number of pixels of the peak B1B is equal to the predetermined number of pixels, the parameter may be corrected or may not be corrected.

Figure 16:
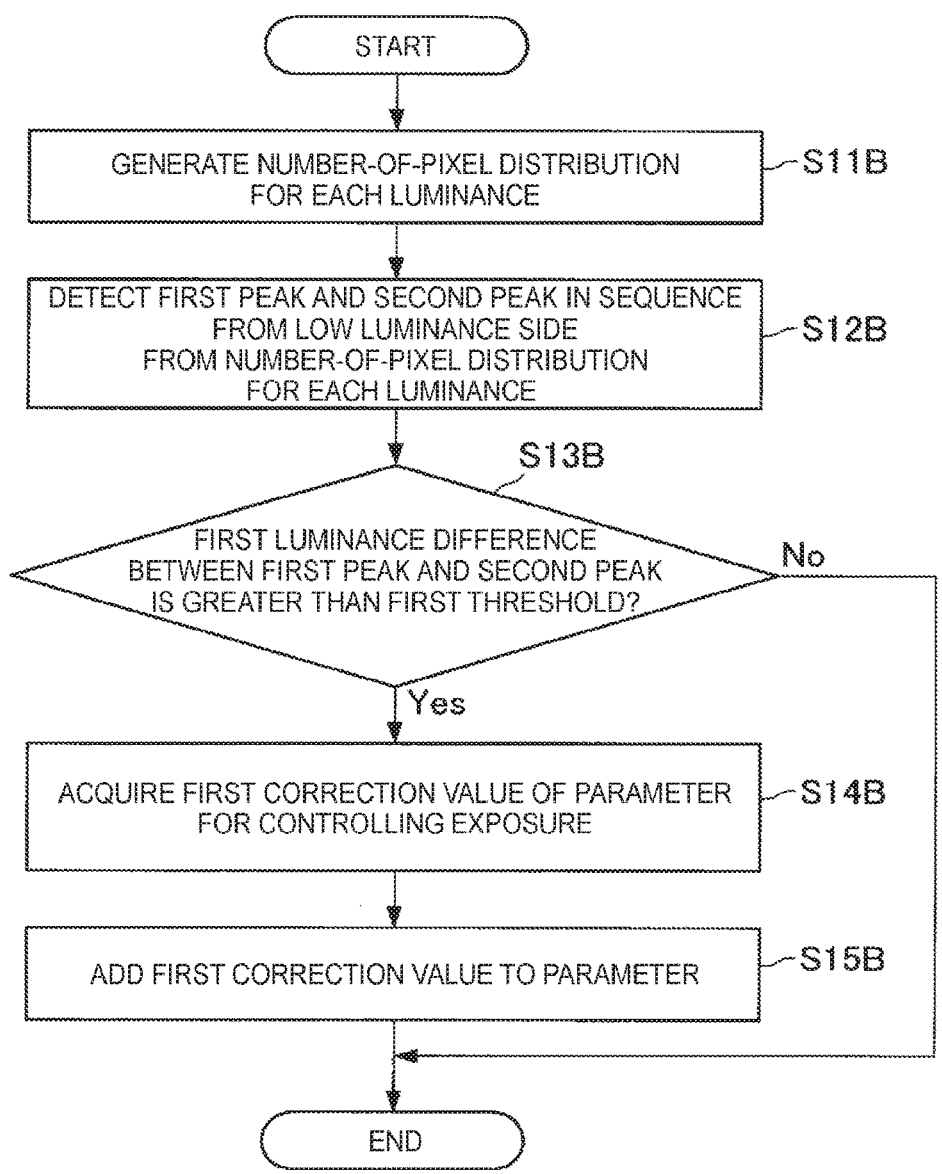
FIG. 16 is a flowchart showing an exemplary operation in a case of detecting two peaks from the low luminance side.

Subsequently, an exemplary operation of the peak detection unit 111B and the exposure control unit 112B as described above will be described. FIG. 16 is a flowchart showing an exemplary operation in the case of detecting two peaks (peak B1B and peak B2B) from the low luminance side. Note that the exemplary operation shown in FIG. 16 is merely an example of operation of the peak detection unit 111B and the exposure control unit 112B. Accordingly, the operation of the peak detection unit 111B and the exposure control unit 112B is not limited to the exemplary operation shown in FIG. 16.

First, as shown in FIG. 16, the peak detection unit 111B generates a number-of-pixel distribution for each luminance in the endoscopic image (S11B). Then, the peak detection unit 111B detects a first peak (peak B1B) and a second peak (peak B2B) in sequence from the low luminance side from the number-of-pixel distribution for each luminance (S12B). Subsequently, in the case that the first luminance difference (luminance difference Df1B) between the first peak (peak B1B) and the second peak (peak B2B) is less than the first threshold ("No" in S13B), the exposure control unit 112B ends the operation.

On the other hand, in the case that the first luminance difference (luminance difference Df1B) between the first peak (peak B1B) and the second peak (peak B2B) is greater than the first threshold ("Yes" in S13B), the exposure control unit 112B acquires a first correction value of the parameter for controlling exposure (S14B), adds the first correction value to the parameter (S15B), and ends the operation. If the exposure control is performed on the basis of the parameter to which the first correction value has been added, the possibility that the observation area Rs1B becomes excessively bright is reduced, and it is possible to further appropriately adjust the luminance of the endoscopic image Im1B.

The case in which the black area Rb1B is generated in the endoscopic image Im1B has been described above.

Here, in a case where an object with higher luminance than inside of a human body (e.g., forceps, gauze or the like) is reflected as a subject, a phenomenon may occur in which the endoscopic image Im1B is partially brightened. In particular, the endoscopic images Im1B are generally captured in a situation that the light source unit 300B and the image sensor 232B are close to each other, or in a situation that the light source unit 300B and the subject are close to each other, so that such a phenomenon is likely to occur. Therefore, there is also an area partially brightened in the endoscopic image Im1B. Hereinafter, an area partially brightened by a reflection of such an object with high luminance in the endoscopic image is also simply referred to as "white area".

Here, there is a case where, due to the occurrence of the white area Rw1B in the endoscopic image Im1B, exposure control may be performed by the automatic exposure control unit 110B so that the luminance of the endoscopic image Im1B becomes excessively low. Thus, the observation area Rs1B may become excessively dark. Accordingly, a technology will be described below which is capable of further appropriately adjusting the luminance of the endoscopic image Im1B by reducing the possibility that the observation area Rs1B becomes excessively dark.

Figure 17:
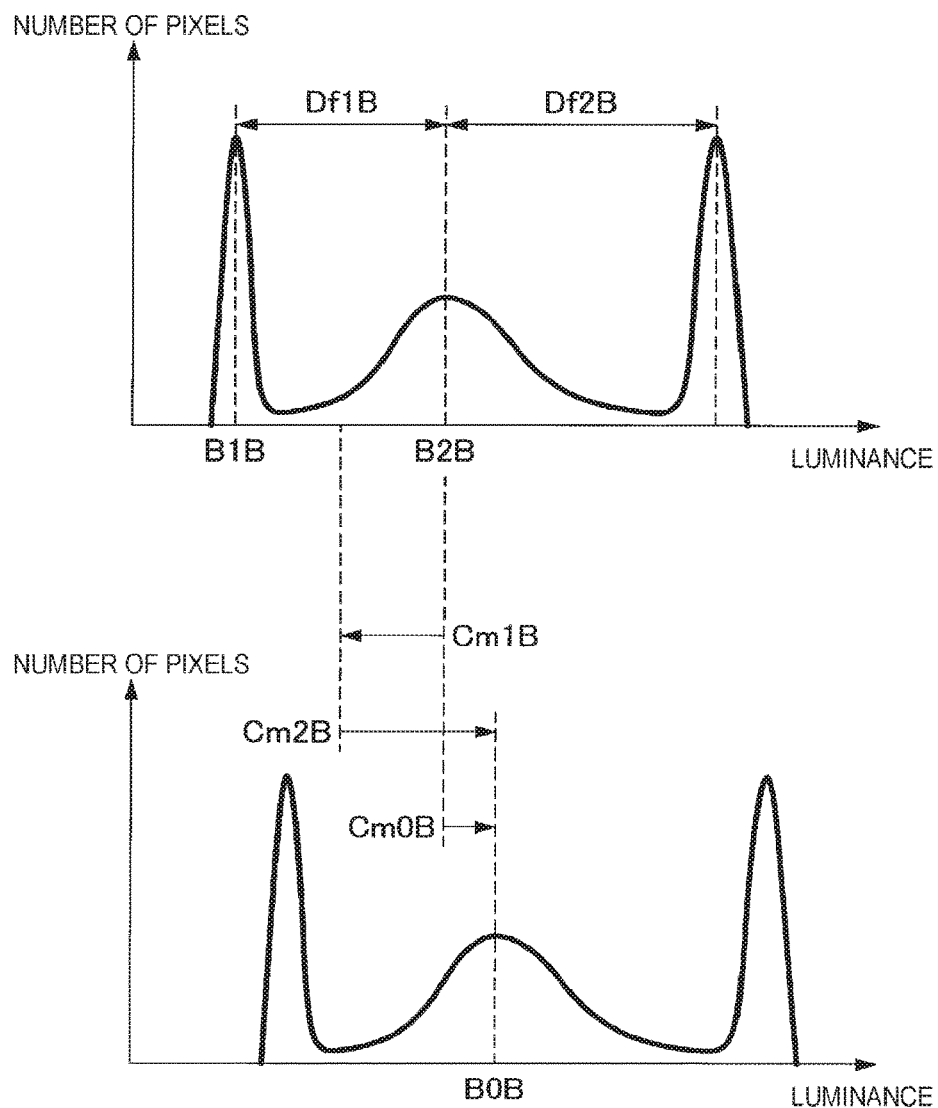
FIG. 17 contains graphs showing another example of a number-of-pixel distribution for each luminance of the endoscopic image.

FIG. 17 contains graphs showing another example of a number-of-pixel distribution for each luminance of the endoscopic image. With reference to FIG. 17, the luminance of the endoscopic image is shown on each horizontal axis, and the number of pixels for each luminance is shown on each vertical axis. Moreover, a first peak (peak B1B) and a second peak (peak B2B) followed by a third peak (hereinafter, also referred to as "peak B3B") are disposed in sequence from the low luminance side. The numbers of pixels at the peak B1B, the peak B2B and the peak B3B are shown as "N1B", "N2B" and "N3B", respectively.

First, the peak detection unit 111B detects the peak B3B on the higher luminance side of the peak B2B from the number-of-pixel distribution for each luminance of the endoscopic image. Then, in the case that the peak B3B belongs to a white area Rw1B, and the peak B2B belongs to the observation area Rs1B, it is assumed that the brightness of the white area Rw1B changes depending on the luminance difference (second luminance difference) Df2B between the peak B3B and the peak B2B. Thus, the exposure control unit 112B may perform exposure control on the basis of the luminance difference Df1B and the luminance difference (second luminance difference) Df2B between the peak B3B and the peak B2B. That makes it possible to further appropriately adjust the luminance of the endoscopic image Im1B by reducing a possibility that the observation area Rs1B becomes excessively dark.

For example, the exposure control unit 112B may acquire a correction value of the parameter (hereinafter, also referred to as "second correction value") on the basis of the luminance difference Df2B, correct the parameter on the basis of the first correction value and the second correction value, and perform exposure control on the basis of the corrected parameter. The exposure control unit 112B may correct the parameter by adding the first correction value and the second correction value to the parameter. In FIG. 17, an example is shown in which the peak B2B moves to the position of the peak B0B as a result of the exposure control performed on the basis of the corrected parameter (the example is shown in which the position of the peak B2B has moved by the sum "Cm0B" of "Cm1B" and "Cm2B").

The method of acquiring the second correction value is not limited in particular. For example, the exposure control unit 112B may acquire the second correction value corresponding to the luminance difference Df2B from a table, or may acquire the second correction value by calculation on the basis of the luminance difference Df2B. The method of acquiring the second correction value by calculation on the basis of the luminance difference Df2B is also not limited in particular. For example, the exposure control unit 112B may calculate the second correction value from the luminance difference Df2B by assuming that the second correction value linearly changes with respect to the luminance difference Df2B.

Moreover, the exposure control unit 112B may correct the parameter in the case that the luminance difference Df2B is greater than a threshold (hereinafter, also referred to as "second threshold"), while not correcting the parameter in the case that the luminance difference Df2B is less than the second threshold. This is because in the case that the luminance difference Df2B is less than the second threshold, the exposure control is less likely to be performed so that the luminance of the endoscopic image Im1B becomes excessively low. Note that in the case that the luminance difference Df2B is equal to the second threshold, the parameter may be corrected or may not be corrected.

Moreover, the exposure control unit 112B may correct the parameter in the case that the number of pixels of the peak B3B exceeds a predetermined number of pixels, while not correcting the parameter in the case that the number of pixels of the peak B3B does not exceed the predetermined number of pixels. This is because in the case that the number of pixels of the peak B3B does not exceed the predetermined number of pixels, the exposure control is less likely to be performed so that the luminance of the endoscopic image Im1B becomes excessively low. Note that in the case that the number of pixels of the peak B3B is equal to the predetermined number of pixels, the parameter may be corrected or may not be corrected.

Figure 18:
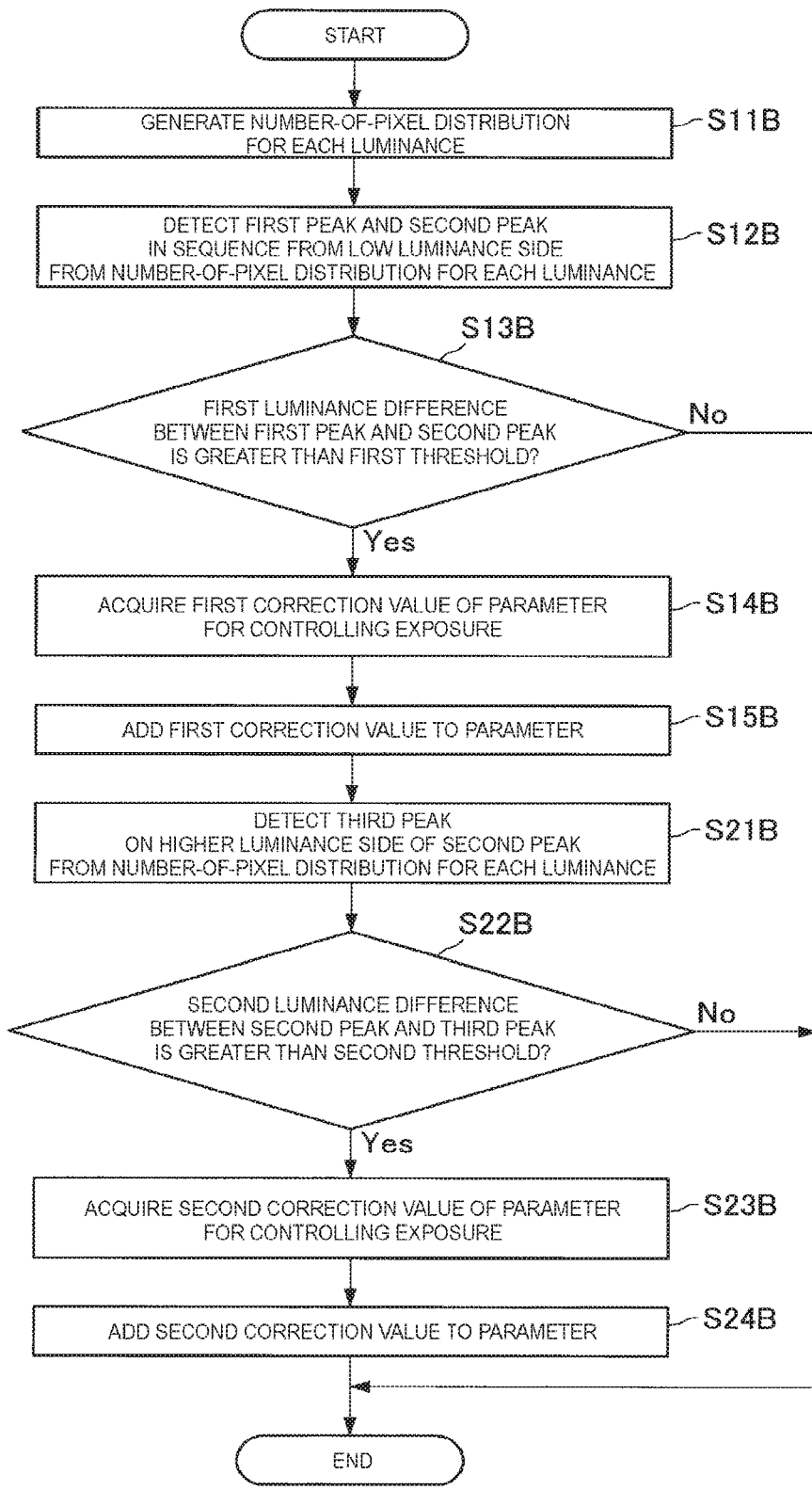
FIG. 18 is a flowchart showing an exemplary operation in a case of detecting three peaks from the low luminance side.

Subsequently, an exemplary operation of the peak detection unit 111B and the exposure control unit 112B as described above will be described. FIG. 18 is a flowchart showing an exemplary operation in the case of detecting three peaks (peak B1B, peak B2B and peak B3B) from the low luminance side. Note that the exemplary operation shown in FIG. 18 is merely an example of operation of the peak detection unit 111B and the exposure control unit 112B. Accordingly, the operation of the peak detection unit 111B and the exposure control unit 112B is not limited to the exemplary operation shown in FIG. 18.

S11B to S15B shown in FIG. 18 are executed as with S11B to S15B shown in FIG. 16. Subsequent to S15B, the peak detection unit 111B detects the third peak (peak B3B) on the higher luminance side of the second peak (peak B2B from a number-of-pixel distribution for each luminance (S21B). Subsequently, in the case that the second luminance difference (luminance difference Df2B) between the third peak (peak B3B) and the second peak (peak B2B) is less than the second threshold ("No" in S22B), the exposure control unit 112B ends the operation.

On the other hand, in the case that the second luminance difference (luminance difference Df2B) between the third peak (peak B3B) and the second peak (peak B2B) is greater than the second threshold ("Yes" in S22B), the exposure control unit 112B acquires the second correction value of the parameter for controlling exposure (S23B), adds the second correction value to the parameter (S24B), and ends the operation. If the exposure control is performed on the basis of the parameter to which the second correction value has been added, the possibility that the observation area Rs1B becomes excessively dark is reduced, and it is possible to further appropriately adjust the luminance of the endoscopic image Im1B.

The case in which the white area Rw1B is generated in the endoscopic image Im1B has been described above. Moreover, the detailed function of the automatic exposure control unit 110B has been described.

5. CONCLUSION

As described above, according to the embodiment of the present disclosure, the image processing device 100B is provided which includes the peak detection unit 111B configured to detect the first peak (peak B1B) and the second peak (peak B2B) in sequence from the low luminance side from the number-of-pixel distribution for each luminance of the endoscopic image Im1B based on imaging by the image sensor 232B, and the exposure control unit 112B configured to perform exposure control on the basis of the luminance difference Df1B between the first peak and the second peak. According to such a configuration, it is possible to further appropriately adjust the luminance of the endoscopic image Im1B by reducing the possibility that the observation area Rs1B becomes excessively bright.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An image processing device including:

a peak detection unit configured to detect a first peak and a second peak in sequence from a low luminance side from a number-of-pixel distribution for each luminance of an endoscopic image based on imaging by an image sensor; and an exposure control unit configured to perform exposure control on a basis of a first luminance difference between the first peak and the second peak.

(2)

The image processing device according to (1), in which the exposure control unit acquires a first correction value of a parameter for controlling exposure on a basis of the first luminance difference, corrects the parameter on a basis of the first correction value, and performs the exposure control on a basis of the corrected parameter.

(3)

The image processing device according to (2), in which the exposure control unit corrects the parameter by adding the first correction value to the parameter.

(4)

The image processing device according to (2) or (3), in which the exposure control unit acquires the first correction value corresponding to the first luminance difference from a table.

(5)

The image processing device according to (2) or (3), in which the exposure control unit acquires the first correction value by calculation on a basis of the first luminance difference.

(6)

The image processing device according to (5), in which the exposure control unit calculates the first correction value from the first luminance difference by assuming that the first correction value linearly changes with respect to the first luminance difference.

(7)

The image processing device according to any one of (1) to (6), in which the exposure control unit performs the exposure control in a case that the first luminance difference is greater than a threshold.

(8)

The image processing device according to any one of (1) to (7), in which the exposure control unit performs the exposure control in a case that the number of pixels of the first peak exceeds a predetermined number of pixels.

(9)

The image processing device according to any one of (2) to (6), in which the peak detection unit detects a third peak on a higher luminance side of the second peak, and the exposure control unit performs the exposure control on a basis of the first luminance difference and a second luminance difference between the second peak and the third peak.

(10)

The image processing device according to (9), in which the exposure control unit acquires a second correction value of the parameter on a basis of the second luminance difference, corrects the parameter on a basis of the first correction value and the second correction value, and performs the exposure control on a basis of the corrected parameter.

(11)

The image processing device according to (10), in which the exposure control unit corrects the parameter by adding the first correction value and the second correction value to the parameter.

(12)

The image processing device according to any one of (2) to (6), in which the parameter includes at least any one of an electronic shutter speed of the image sensor and a gain by which an analog signal captured by the image sensor is multiplied.

(13)

The image processing device according to any one of (2) to (6), in which the parameter includes brightness of a light source.

(14)

An image processing method including:

detecting a first peak and a second peak in sequence from a low luminance side from a number-of-pixel distribution for each luminance of an endoscopic image based on imaging by an image sensor; and performing exposure control by a processor on a basis of a first luminance difference between the first peak and the second peak.

(15)

A program for causing a computer to function as an image processing device including:

a peak detection unit configured to detect a first peak and a second peak in sequence from a low luminance side from a number-of-pixel distribution for each luminance of an endoscopic image based on imaging by an image sensor; and an exposure control unit configured to perform exposure control on a basis of a first luminance difference between the first peak and the second peak.

(16)

An image processing system including:

a light source unit configured to emit light;

an image sensor configured to capture an endoscopic image by receiving reflected light of the light emitted by the light source unit; and
    an image processing device including
        a peak detection unit configured to detect a first peak and a second peak in sequence from a low luminance side from a number-of-pixel distribution for each luminance of the endoscopic image, and
        an exposure control unit configured to perform exposure control on a basis of a first luminance difference between the first peak and the second peak.

REFERENCE SIGNS LIST 1A image processing system
100A image processing device
110A automatic exposure control unit
111A peak detection unit
112A exposure control unit
120A image processing unit
130A control unit
200A insertion unit
210A light guide
220A illumination lens
230A imaging unit
231A objective lens
232A image sensor
233A A/D conversion unit
240A memory
300A light source unit
310A white light source
320A condenser lens
400A display unit
500A operation unit
B0A peak
B1A peak (first peak)
B2A peak (second peak)
B3A peak (third peak)
Df1A luminance difference
Df2A luminance difference
Im1A endoscopic image
Rb1A black area
Rs1A observation area
Rw1A white area
SuA subject
1B image processing system
100B image processing device
110B automatic exposure control unit
111B peak detection unit
112B exposure control unit
120B image processing unit
130B control unit
200B insertion unit
210B light guide
220B illumination lens
230B imaging unit
231B objective lens
232B image sensor
233B A/D conversion unit
240B memory
300B light source unit
310B white light source
320B condenser lens
400B display unit
500B operation unit
B0B peak
B1B peak (first peak)
B2B peak (second peak)
B3B peak (third peak)
Df1B luminance difference
Df2B luminance difference
Im1B endoscopic image
Rb1B black area
Rs1B observation area
Rw1B white area
SuB subject

The invention claimed is:

1. An image processing device for an endoscopic image, the image processing device comprising:
    processing circuitry configured to
        detect a first luminance value and a second luminance value based on a number-of-pixel distribution for a plurality of luminance values of the endoscopic image, the endoscopic image being generated based on imaging information from an image sensor, and the first luminance value corresponding to a vignetted area of the endoscopic image; and
        perform exposure control based on a first luminance difference between the first luminance value and the second luminance value.

2. The image processing device according to claim 1, wherein the processing circuitry is configured to perform the exposure control by acquiring a first correction value of a parameter for controlling exposure based on the first luminance difference, and correcting the parameter based on the first correction value.

3. The image processing device according to claim 2, wherein the processing circuitry is configured to correct the parameter by adding the first correction value to the parameter.

4. The image processing device according to claim 2, wherein the processing circuitry is configured to acquire the first correction value corresponding to the first luminance difference from a table.

5. The image processing device according to claim 2, wherein the processing circuitry is configured to acquire the first correction value by a calculation that is based on the first luminance difference.

6. The image processing device according to claim 5, wherein the processing circuitry is configured to calculate the first correction value from the first luminance difference based on a linear relationship between the first correction value and the first luminance difference.

7. The image processing device according to claim 1, wherein the processing circuitry is configured to perform the exposure control in a case that the first luminance difference is greater than a threshold.

8. The image processing device according to claim 1, wherein the processing circuitry is configured to perform the exposure control in a case that the number of pixels of the first luminance value exceeds a predetermined number of pixels.

9. The image processing device according to claim 2, wherein the processing circuitry is configured to
    detect a third luminance value that is lower than the second luminance value, and
    perform the exposure control based on the first luminance difference and a second luminance difference between the second luminance value and the third luminance value.

10. The image processing device according to claim 9, wherein the processing circuitry is configured to perform the exposure control by acquiring a second correction value of the parameter based on the second luminance difference, and correcting the parameter based on the first correction value and the second correction value.

11. The image processing device according to claim 10, wherein the processing circuitry is configured to correct the parameter by adding the first correction value and the second correction value to the parameter.

12. The image processing device according to claim 2, wherein the parameter includes at least any one of an electronic shutter speed of the image sensor or a gain by which an analog signal captured by the image sensor is multiplied.

13. The image processing device according to claim 2, wherein the parameter includes brightness of a light source.

14. An image processing method for an endoscopic image, the image processing method comprising:
  detecting, by processing circuitry of an image processing device, a first luminance value and a second luminance value based on a number-of-pixel distribution for each of a plurality of luminance values of the endoscopic image, the endoscopic image being generated based on imaging information from an image sensor, the first luminance value corresponding to a vignetted area of the endoscopic image; and
  performing exposure control, by the processing circuitry, based on a first luminance difference between the first luminance value and the second luminance value.

15. A non-transitory computer-readable medium storing a program which when executed by a computer causes the computer to perform an image processing method for an endoscopic image, the image processing method comprising:
  detecting a first luminance value and a second luminance value based on a number-of-pixel distribution for each of a plurality of luminance values of the endoscopic image, the endoscopic image being generated based on imaging information from an image sensor, and the first luminance value corresponding to a vignetted area of the endoscopic image; and
  performing exposure control based on a first luminance difference between the first luminance value and the second luminance value.

16. An image processing system for an endoscopic image, the image processing system comprising:
  a light source configured to emit light;
  an image sensor configured to generate imaging information based on reflected light of the light emitted by the light source; and
  an image processing device including processing circuitry, the processing circuitry being configured to
    detect a first luminance value and a second luminance value based on a number-of-pixel distribution for each of a plurality of luminance values of the endoscopic image, the endoscopic image being generated based on imaging information from an image sensor, and the first luminance value corresponding to a vignetted area of the endoscopic image, and
    perform exposure control based on a first luminance difference between the first luminance value and the second luminance value.

* * * * *